(12) United States Patent
Daniels et al.

(10) Patent No.: US 7,074,224 B2
(45) Date of Patent: Jul. 11, 2006

(54) MODULAR TAPERED REAMER FOR BONE PREPARATION AND ASSOCIATED METHOD

(75) Inventors: David Wayne Daniels, Warsaw, IN (US); Charles Wesley Jaggers, Warsaw, IN (US); Kimberly Ann Dwyer, Fort Wayne, IN (US); David William Morrow, Fort Wayne, IN (US); Brad Alan Parker, Warsaw, IN (US); Daniel J. Berry, Rochester, MN (US)

(73) Assignee: Depuy Products, Inc., Warsaw, IN (US)

( * ) Notice: Subject to any disclaimer, the term of this patent is extended or adjusted under 35 U.S.C. 154(b) by 355 days.

(21) Appl. No.: 10/606,303

(22) Filed: Jun. 25, 2003

(65) Prior Publication Data

US 2004/0267266 A1 Dec. 30, 2004

(51) Int. Cl.
*A61B 17/00* (2006.01)
(52) U.S. Cl. ...................................................... 606/80
(58) Field of Classification Search ................ 606/79, 606/80, 84, 85
See application file for complete search history.

(56) References Cited

U.S. PATENT DOCUMENTS

| | | | |
|---|---|---|---|
| 3,810,312 A | 5/1974 | Carson | |
| 4,716,894 A | 1/1988 | Lazzeri et al. | |
| 4,917,530 A | 4/1990 | Engelhardt et al. | |
| 4,969,911 A | 11/1990 | Greene | |
| 5,002,578 A * | 3/1991 | Luman ..................... 623/22.42 |
| 5,002,581 A | 3/1991 | Paxson et al. | |
| 5,100,407 A | 3/1992 | Conrad et al. | |
| 5,135,529 A | 8/1992 | Paxson et al. | |
| 5,197,989 A | 3/1993 | Hinckfuss et al. | |
| 5,201,882 A | 4/1993 | Paxson | |
| 5,370,706 A | 12/1994 | Bolesky et al. | |
| 5,507,824 A | 4/1996 | Lennox | |
| 5,507,830 A | 4/1996 | DeMane et al. | |
| 5,601,567 A | 2/1997 | Swajger et al. | |
| 5,607,431 A | 3/1997 | Dudasik et al. | |
| 5,645,607 A | 7/1997 | Hickey | |
| 5,658,349 A | 8/1997 | Brooks et al. | |
| 5,697,932 A * | 12/1997 | Smith et al. ................... 606/80 |
| 5,702,487 A * | 12/1997 | Averill et al. ............. 623/23.35 |
| 5,728,128 A | 3/1998 | Crickenberger et al. | |
| 5,766,261 A | 6/1998 | Neal et al. | |
| 5,776,200 A | 7/1998 | Johnson et al. | |
| 5,792,143 A | 8/1998 | Samuelson et al. | |
| 5,810,829 A | 9/1998 | Elliott et al. | |

(Continued)

FOREIGN PATENT DOCUMENTS

WO      WO 98/15739      5/1996

*Primary Examiner*—Eduardo C. Robert
*Assistant Examiner*—Michael J. Araj
(74) *Attorney, Agent, or Firm*—John S. Wagley

(57) ABSTRACT

A kit (400) for use in performing joint arthroplasty is provided. The kit (400) includes a trial (12) and a reamer (2). The reamer (2) is for preparing a cavity (4) in the intramedullary canal (8) of a long bone (8) with the use of a driver (10) and to assist in performing a trial reduction. The reamer (2) includes a first portion (14) for placement at least partially in the cavity (4) of the long bone (8) and a second portion (16) operably connected to the first portion (14). The reamer (2) is removably connected to the driver (10) to rotate the reamer (2). The trial (12) is removably attachable to the reamer (2).

3 Claims, 33 Drawing Sheets

U.S. PATENT DOCUMENTS

| | | |
|---|---|---|
| 5,810,830 A | 9/1998 | Noble et al. |
| 5,858,020 A | 1/1999 | Johnson et al. |
| 5,860,969 A | 1/1999 | White et al. |
| 5,876,459 A | 3/1999 | Powell |
| 5,879,391 A | 3/1999 | Slamin |
| 5,906,644 A | 5/1999 | Powell |
| 5,919,195 A | 7/1999 | Wilson et al. |
| 5,935,172 A | 8/1999 | Ochoa et al. |
| 5,951,606 A | 9/1999 | Burke |
| 5,976,147 A | 11/1999 | LaSalle et al. |
| 5,976,188 A | 11/1999 | Dextradeur et al. |
| 5,993,455 A | 11/1999 | Noble |
| 6,045,556 A | 4/2000 | Cohen |
| 6,071,311 A | 6/2000 | O'Neil et al. |
| 6,080,162 A | 6/2000 | Dye et al. |
| 6,117,138 A | 9/2000 | Burrows et al. |
| 6,126,694 A | 10/2000 | Gray, Jr. |
| 6,179,877 B1 | 1/2001 | Burke |
| 6,193,759 B1 | 2/2001 | Ro et al. |
| 6,197,065 B1 | 3/2001 | Martin et al. |
| 6,206,884 B1 | 3/2001 | Masini |
| 6,224,605 B1 | 5/2001 | Anderson et al. |
| 6,238,435 B1 | 5/2001 | Meulink et al. |
| 6,258,095 B1 | 7/2001 | Lombardo et al. |
| 6,258,097 B1 | 7/2001 | Cook et al. |
| 6,319,286 B1 | 11/2001 | Fernandez et al. |
| 6,332,886 B1 | 12/2001 | Green et al. |
| 6,355,068 B1 | 3/2002 | Doubler et al. |
| 6,361,563 B1 | 3/2002 | Terrill-Grisoni et al. |
| 6,432,110 B1 | 8/2002 | Richelsoph |
| 6,517,581 B1 | 2/2003 | Blamey |
| 6,702,854 B1 * | 3/2004 | Cheal et al. .............. 623/22.42 |
| 2001/0001121 A1 | 5/2001 | Lombardo et al. |
| 2001/0007957 A1 | 7/2001 | Martin et al. |
| 2003/0171816 A1 * | 9/2003 | Scifert et al. ............. 623/22.12 |
| 2004/0015239 A1 * | 1/2004 | Beguec .................... 623/23.26 |
| 2004/0147933 A1 * | 7/2004 | McGovern ................... 606/80 |

* cited by examiner

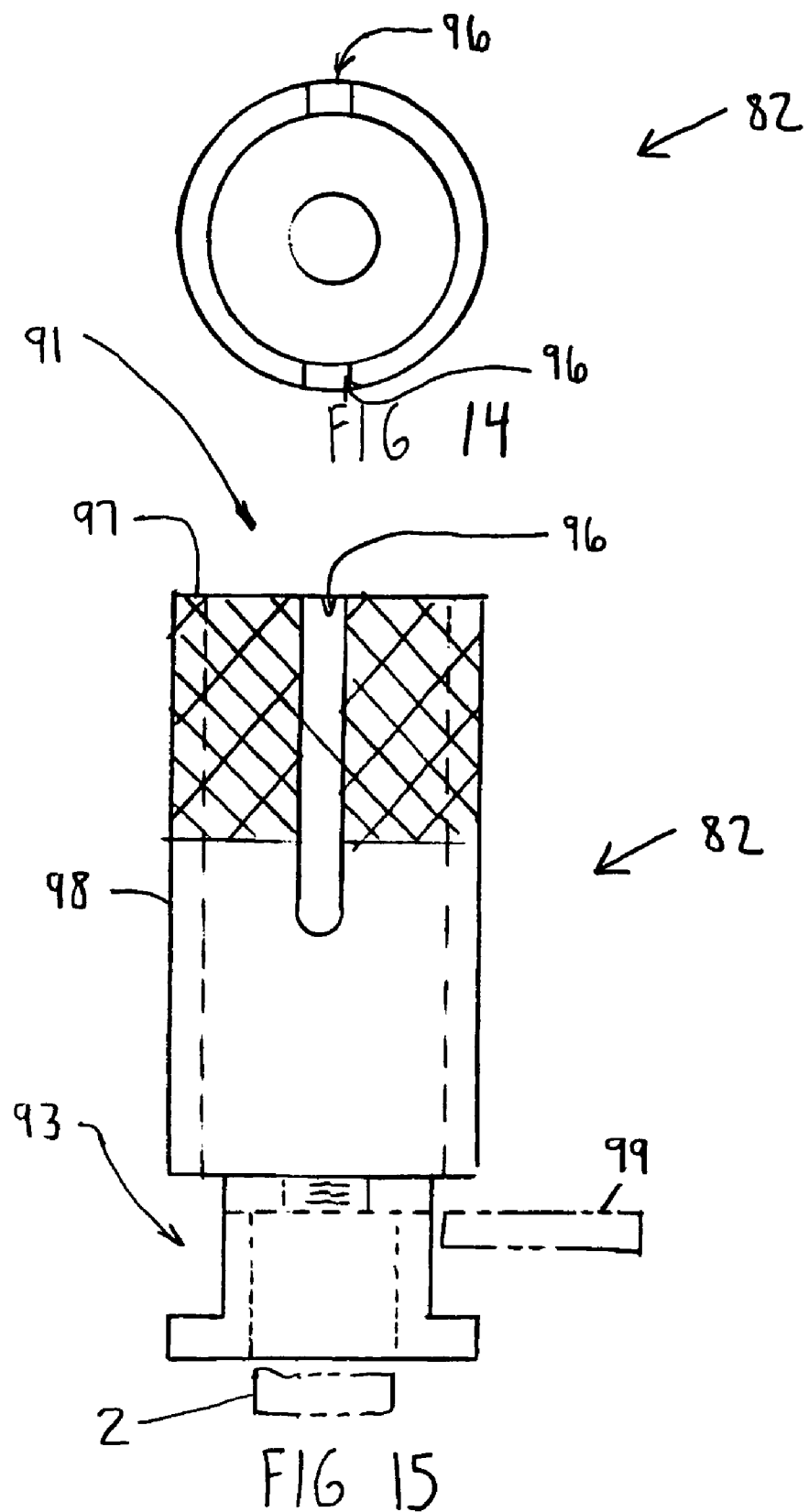

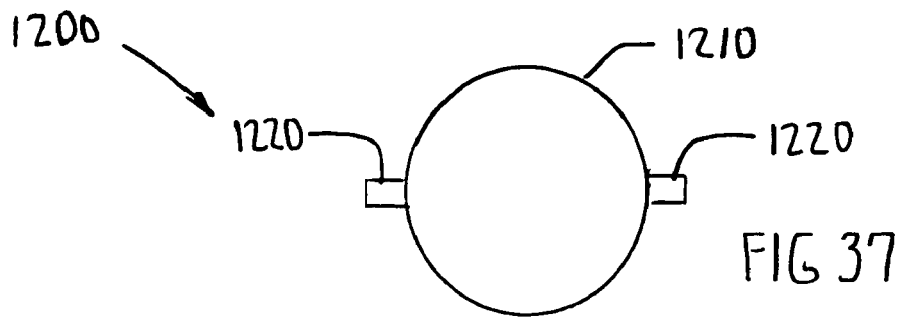
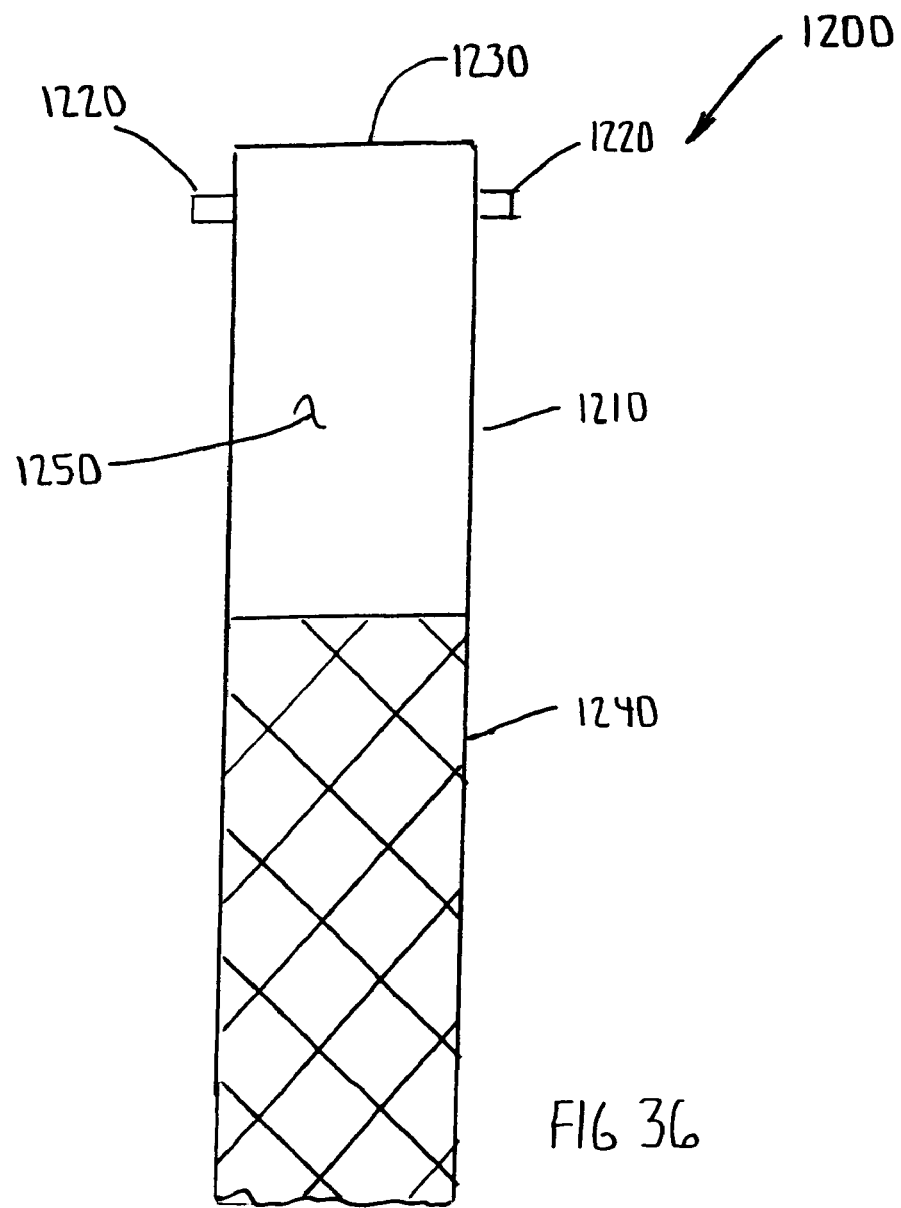

MODULAR TAPERED REAMER FOR BONE PREPARATION AND ASSOCIATED METHOD

CROSS-REFERENCE TO RELATED APPLICATIONS

Cross reference is made to the following applications: DEP 670 entitled "ASSEMBLY TOOL FOR MODULAR IMPLANTS AND ASSOCIATED METHOD" and DEP 5083 entitled "NON-LINEAR REAMER FOR BONE PREPARATION AND ASSOCIATED METHOD" filed concurrently herewith which are incorporated herein by reference.

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

Currently in total hip arthroplasty, a major critical concern is the instability of the joint. Instability is associated with dislocation. Dislocation is particularly a problem in total hip arthroplasty.

Factors related to dislocation include surgical technique, implant design, implant positioning and patient related factors. In total hip arthroplasty, implant systems address this concern by offering a series of products with a range of lateral offsets, neck offsets, head offsets and leg lengths. The combination of these four factors affects the laxity of the soft tissue. By optimizing the biomechanics, the surgeon can provide a patient a stable hip much more resistant to dislocation. In order to accommodate the range of patient arthropometrics, a wide range of hip implant geometries are currently manufactured by DePuy Orthopaedics, Inc., the assignee of the current application, and by other companies. In particular, the S-ROM® total hip systems offered by DePuy Orthopaedics, Inc. include three offsets, three neck lengths, four head lengths and one leg length adjustment. The combination of all these biomechanic options is rather complex.

Anteversion of a total hip system is closely linked to the stability of the joint. Improper version can lead to abnormal biodynamics, dislocation and patient dissatisfaction. Version control is important in all hip stems. However, it is a more challenging issue with the advent of stems with additional modularity.

The prior art has provided for some addressing of the anteversion problem. For example, the current S-ROM® stems have laser markings on the medial stem and the proximal sleeve. This marking enables the surgeon to measure relative alignment between these components. Since the sleeve has infinite anteversion, it is not necessarily oriented relative to a bony landmark that can be used to define anteversion. In fact, the current sleeves are sometimes oriented with the spout pointing directly laterally into the remaining available bone.

Prior art stems may be aligned relative to a patient's bony landmarks. These stems are monolithic. They cannot locate the neck independently of the distal stem. Therefore, the anteversion is limited. Most bowed, monolithic stems are sold in fixed anteversion; for example, at an anteversion of 15 degrees. These monolithic stems have limited flexibility for rotational alignment since the distal stem must follow the bow of the patient's femur and this may not provide an operable biomechanical result.

When a primary or index total joint arthroplasty fails, a revision procedure is performed in which the index devices (some or all) are removed. Quite often the remaining bone is significantly compromised compared to a primary hip procedure. Significant bone loss is observed, often with a lack of bone landmarks typically used for alignment.

In a common step in the surgical procedure known as total hip arthroplasty, a trial or substitute stem is first implanted into the patient. The trial is utilized to verify the selected size and shape of the implant in situ on the patient and the patient is subjected to what is known as a trial reduction. This trial reduction represents moving the joint, including the trial implant through selected typical motions for that joint. Current hip instruments provide a series of trials of different sizes to help the surgeon assess the fit and position of the implant. Trials, which are also known as provisionals, allow the surgeon to perform a trial reduction to assess the suitability of the implant and implant's stability prior to final implant selection. The trial also duplicates the implant's geometry. In order to reduce inventory costs and complexity, many trialing systems are modular. For example, in the Excel™ Instrument System, a product of DePuy Orthopaedics, Inc., there is a series of broaches and a series of neck trials that can be mixed and matched to represent the full range of implants. There is a single fixed relationship between a broach and a neck trial, because these trials represent a system of monolithic stem implants.

Likewise, in the current S-ROM® instrument systems provided by DePuy Orthopaedics, Inc., there are neck trials, proximal body trials, distal stem trials, head trials and sleeve trials. By combining all of these components, the implant is represented. Since the S-ROM® stem is modular and includes a stem and a sleeve, the angular relationship or relative anteversion between the neck and the sleeve is independent and represented by teeth mating between the neck and the proximal body trial. The proximal body trial has fixed transverse bolts that are keyed to the sleeve in the trialing for straight, primary stems. The long stem trials do not have the transverse bolts and are thus not rotationally stable during trial reduction and therefore are not always used by the surgeon.

With the introduction of additional implant modularity, the need for independent positioning of the distal stem, proximal body and any sleeve which comprise the implants is required. Currently bowed, monolithic stems are offered with a fixed amount of anteversion, typically 15 degrees.

When performing joint arthroplasty, the long bone is resected and the cavity is prepared for the prosthetic stem.

The canal is prepared by, for example, reamers, for example, a tapered reamer. After the canal has been reamed, a trial prosthesis is positioned in the cavity. A trial reduction is then performed with that trial. If the trial reduction is successful, the trial is removed and an implant corresponding to that trial is placed in the cavity. Each step of the process, for example, the positioning of the trial after the reaming and the positioning of the implant after the trialing provides for an additional location error in the proper placement of the prosthesis, as well as additional time for the surgical procedure. There thus remains a need for improving the positioning of a prosthesis while reducing the surgical time in which the patient is at risk.

U.S. patent application Ser. No. 10/327,187 entitled "ADJUSTABLE BIOMECHANICAL TEMPLATING & RESECTION INSTRUMENT AND ASSOCIATED METHOD", U.S. patent application Ser. No. 10/327,196 entitled "ALIGNMENT DEVICE FOR MODULAR IMPLANTS AND METHOD" and U.S. patent application Ser. No. 10/327,527 entitled "INSTRUMENT AND ASSOCIATED METHOD OF TRIALING FOR MODULAR HIP STEMS" are hereby incorporated in their entireties by reference.

SUMMARY OF THE INVENTION

The applicants have found that the surgeon will have the greatest certainty that the trial reduction biomechanics are correct if the surgeon can do the trial reduction with the reamer still in position in the canal. Systems in use today, however, require the user to remove the reamer and insert a trial stem to do a trial reduction. A trial reduction from the reamer ensures that the relative references are maintained. The applicants have determined that to permit the trial reduction off the reamer, the proximal attachment linking the reamer to the power source may be modular. The drive shaft for the reamer should preferably be long enough to reach outside of the patient. The applicants have been able to overcome the problem that a femoral trial long enough to work with the drive shaft will affect the biomechanics of the trial reduction.

The applicants have discovered that by providing a modular connection for which the driver may be modularly connected to the cutting edge of the reamer, the distal or cutting edge portion of the reamer may be separated from the driver while the reamer is still in position in the patient. A proximal trial portion may then be placed on the in-position reamer located in the femoral canal. The distal reamer and the proximal trial may then be used as a trial to perform a trial reduction on the patient. The use of the combination of a proximal reamer and distal trial provides for a reduction in the steps necessary to go from reaming to the implant, thus improving the positioning of the final implant. The positioning of a proximal trial on a distal reamer also reduces the steps necessary in performing an arthroplasty and reduces the amount of time the patient is under the anesthesia.

According to one embodiment of the present invention, there is provided a kit for use in performing joint arthroplasty. The kit includes a trial and a reamer. The reamer is for preparing a cavity in the intramedullary canal of a long bone with the use of a driver and to assist in performing a trial reduction. The reamer includes a first portion for placement at least partially in the cavity of the long bone and a second portion operably connected to the first portion. The reamer is removably connected to the driver to rotate the reamer. The trial is removably attachable to the reamer.

According to another embodiment of the present invention there is provided a kit for use in performing hip joint arthroplasty, the kit is used to prepare a cavity in the femoral canal of a femur with the use of a driver. The kit is also used to assist in performing a trial reduction. The kit includes a hip femoral component trial and a reamer. The reamer is used for preparation of the cavity in the femoral canal. The reamer includes a first portion for placement at least partially in the cavity of the femur and a second portion connectable to the driver. The trial and the driver are removably attachable to the reamer, so that the reamer and the driver can be assembled to prepare the cavity and so that the reamer and the trial can be assembled to form a hip femoral component trial assembly without the removal of the reamer from the cavity.

According to yet another embodiment of the present invention there is provided a reamer for preparing a cavity in the intramedullary canal of a long bone with the use of a driver and for cooperation with an implant trial to assist in performing a trial reduction. The reamer includes a first portion for preparation of the cavity in the canal. The first portion is adapted for placement at least partially in the cavity of the long bone. The reamer also includes a second portion operably connected to the first portion. The second portion is connectable to the driver to rotate the reamer. The reamer is removably attachable to the trial and to the driver.

According to a further embodiment of the present invention, there is provided a method for providing joint arthroplasty. The method includes the steps of resecting a long bone, opening a medullary canal of the long bone, providing a reamer including a surface for the removal of bone, attaching a driver to the reamer, positioning the reamer in the canal, reaming a cavity in the canal with the reamer, detaching the driver from the reamer, providing a trial, attaching the trial to the reamer, and performing a trial reduction.

The technical advantages of the present invention include the reduction of dislocations by improving the stability of the joint. For example, according to one aspect of the present invention, a proximal trial is placed on a reamer which remains in the canal after the reaming has been performed. The trialing can thus be performed from the reamer. The added step of removing the reamer and placing the trial in the hole prepared by the reamer is eliminated and the resultant reduction inaccuracy of the position of the trial is thereby eliminated. Thus, the positioning of the trial with respect to the reamed cavity is improved. Because of the improved positioning of the trial, the stability of the joint is improved and dislocation is reduced. Thus, the present invention provides for improved stability and positioning of the joint.

Another technical advantage of the present invention includes the ability of the modular reamer of the present invention to provide optimal biomechanics. Because of the shallow taper angle, axial positioning is difficult. The present invention provides for improved positioning of the prosthesis and an optimization of the soft tissue position and the reduction of soft tissue laxity. For example, according to one aspect of the present invention, the modular reamer permits the mounting of a proximal trial on the reamer while the tapered reamer is still in position in the canal. The surgeon has the greater certainty that the trial reduction biomechanics are correct if he can do the trial reduction off the reamer. This ensures that the relative references are maintained. By eliminating the additional step of removing the reamer and implanting a distal trial as well as the proximal trial, the accuracy of the trial and resultant implant positioning is improved. The improved positioning of the prosthesis provides for improved soft tissue positioning and optimum biomechanics. Thus, the present invention provides for optimum biomechanics.

Another technical advantage of the present invention includes improved anteversion or the angular orientation of the joint in the body. For example, according to another aspect of the present invention, the driver may be separated from the distal reamer while the distal reamer is still in position in the bone canal and a proximal trial may be positioned on the reamer. The trialing of the prosthesis on the reamer allows for relative rotational position and provides for improved accuracy of the positioning of the trial and therefore improved anteversion of the joint in the body. Thus, the present invention provides for improved anteversion of the joint in the body.

Yet another technical advantage of the present invention includes a reduction in the surgery time, which reduces the time the patient is at risk for surgery related complications. For example, according to one aspect of the present invention, the driver may be removed from the distal reamer while the distal reamer is still in position in the canal and a proximal trial may be positioned on the distal reamer. The prosthesis may thus be trialed off the reamer. Thus, the additional step of removing the reamer and positioning a distal trial in the cavity is eliminated thereby reducing the steps necessary for the procedure and the corresponding additional time for the removal of the reamer and the placement of the distal trial. Thus, the present invention provides for reduced surgery time and reduced patient complications during surgery.

Yet another technical advantage of the present invention includes the ability to use the medullary canal of the long bone or femur as a reference for the proper positioning of the implant, particularly when a revision procedure is performed in which the normal bone are landmarks, such as the greater and lesser trochanter, (some or all) are no longer present. For example, according to one aspect of the present invention, a proximal trial is placed on a reamer which is used to ream the medullary canal of the long bone or femur. The reamer remains in the canal after the reaming has been performed. The trialing can thus be performed from the reamer. Thus, the present invention provides for the use of the medullary canal of the long bone or femur as a reference for the proper positioning of the implant.

By being able to trial off the reamers, one can eliminate a whole tray of instruments which reduces cost and system complexity.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 10 is a plan view of the hip stem trail and modular reamer assembly of FIG. 9;

FIG. 14 is a top view of a nut for use with the modular reamer assembly of FIG. 9;

FIG. 15 is a plan view of the nut for use with the modular reamer assembly of FIG. 9;

FIG. 36 is a top view of an tool for use to tighten the nut of FIG. 15; and

FIG. 37 is a plan view of the tool of FIG. 36.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
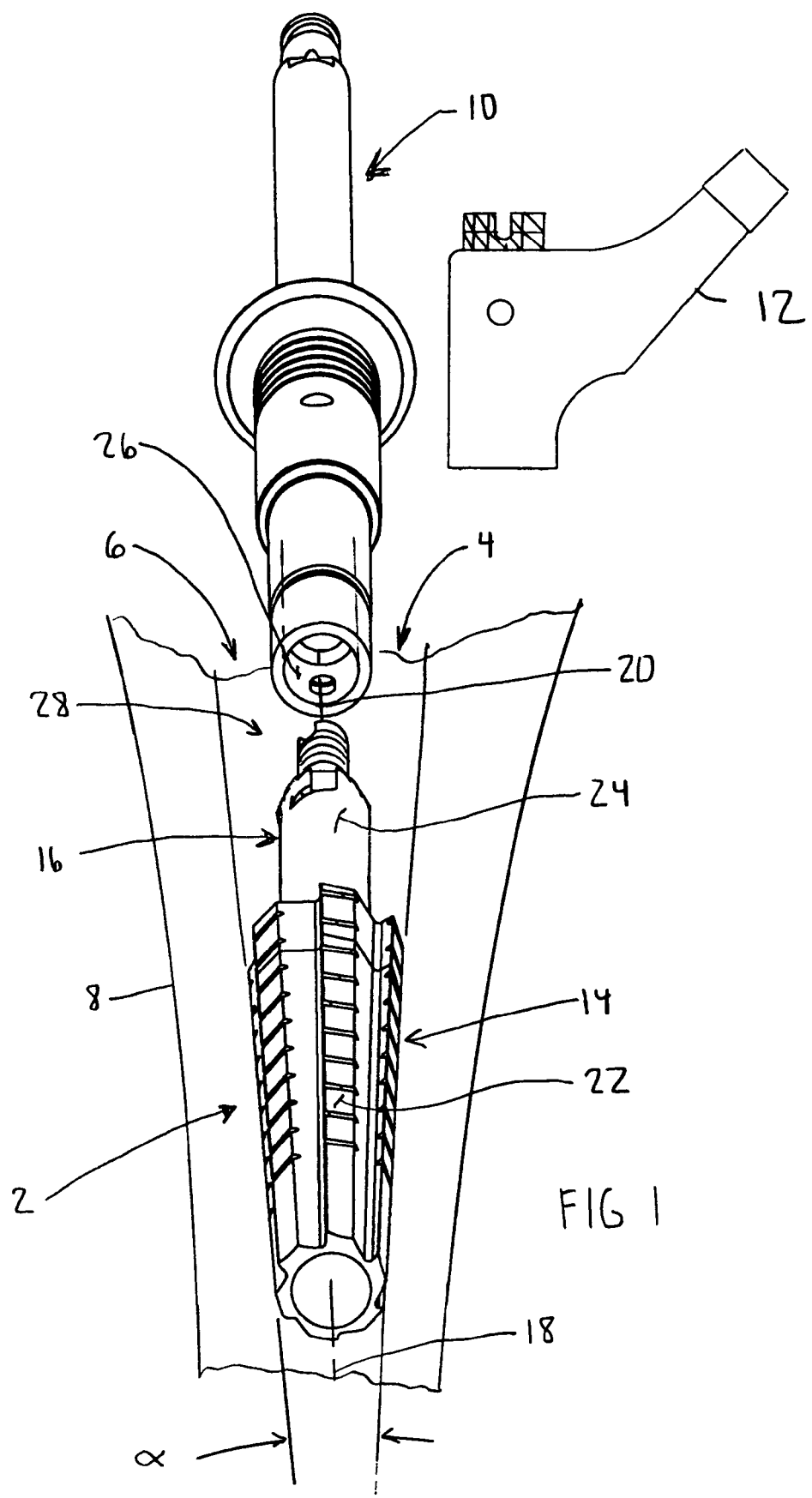
FIG. 1 is an exploded perspective view of a modular reamer assembly in accordance with an embodiment of the present invention and a plan view of a trial for use with the modular reamer.

Referring now to FIG. 1, a reamer 2 according to the present invention is shown. The reamer 2 is utilized for preparing a cavity 4 in the intramedullary canal 6 of a long bone 8 with the use of a driver 10. The reamer 2 cooperates with an implant trial 12 to assist in performing a trial reduction. The reamer 2 includes a first portion 14 for preparation of the cavity 4 in the canal 6. The first portion 14 is adapted for placement at least partially in the cavity 4 of the long bone 8. The reamer 2 further includes a second portion 16 operably connected to the first portion 14. The second portion 16 is also connectable to the driver 10 to rotate the reamer 2. The reamer 2 is removably attachable to the trial 12 and to the driver 10.

As shown in FIG. 1, the first portion 14 of the reamer 2 may define a longitudinal axis 18 of the first portion 14. Similarly, the second portion 16 of the reamer 2 may define a longitudinal axis 20 of the second portion 16. Longitudinal axis 20 of the second portion 16 may be coincident with the longitudinal axis 18 of the first portion 14. As shown in FIG. 1, the reamer 2 may be separable and connectable to the driver 10 and to the trial 12 along the longitudinal axis 18 of the first portion 14.

As shown in FIG. 1, the first portion 14 of the reamer 2 may include a tapered external periphery 22. The tapered external periphery 22 is utilized to prepare a tapered cavity 4 in the canal 6. The second portion 16 of the reamer 2 includes an external periphery 24. The external periphery 24 may mate with, for example, an internal periphery 26 formed on the driver 10.

The external periphery 24 of the second portion 16 of the reamer 2 is, as shown, cylindrical. It shall be appreciated that the external periphery 24 may be tapered. If periphery 24 is tapered then internal periphery 26 of driver 10 would be likewise tapered.

If the external periphery 4 of the second portion 16 of the reamer 2 is tapered, the taper may assist in providing a secure fit between the reamer 2 and either the driver 10 or the trial 12. The connection results in a very small outside diameter of the distal end of drive shaft 10, so that device can be used on small sizes.

Referring again to FIG. 1, the reamer 2 may further include a locking feature 28 adapted to lock the trial 12 and the driver 10 to the reamer 2.

As shown in FIG. 1, the periphery 22 of the first portion 14 of the reamer 2 may be defined by an included angle α. The angle α may be any angle conforming to the angle of the distal stem of the prosthetic and any suitable angle capable of providing secure engagement of the prosthesis.

If the external periphery of the second portion (not shown) of the reamer is tapered, the periphery may be defined by an included angle (not shown). The angle may be any suitable angle capable of providing a secure fit between the reamer and either of the driver or the trial.

While the reamer 2 of the present invention may be well suited to prepare the cavity of any long bone 8, the reamer 2 is particularly well suited for use in a femur. When the long bone 8 is in the form of a femur, the implant trial 12 will be in form of a hip femoral implant trial.

Figure 2:
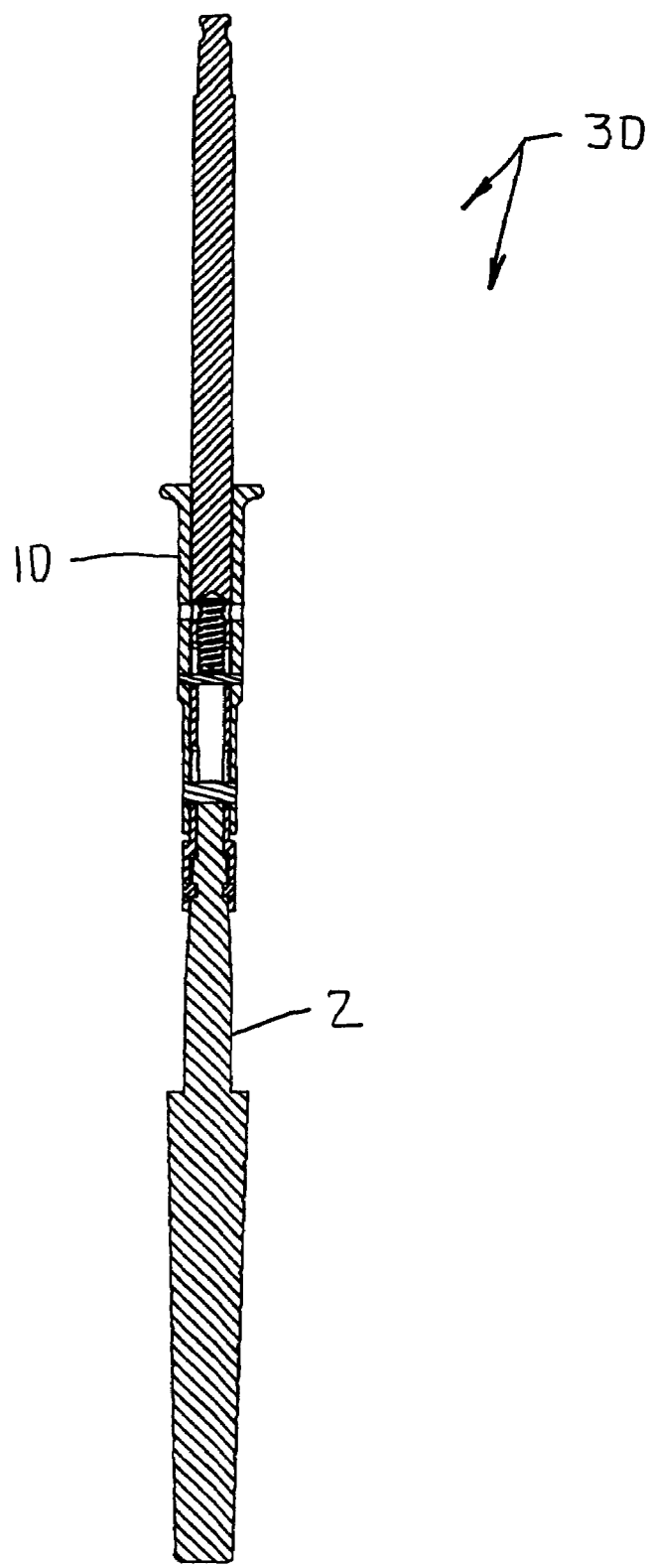
FIG. 2 is a cross sectional view of the modular reamer assembly of FIG. 1.
Figure 3:
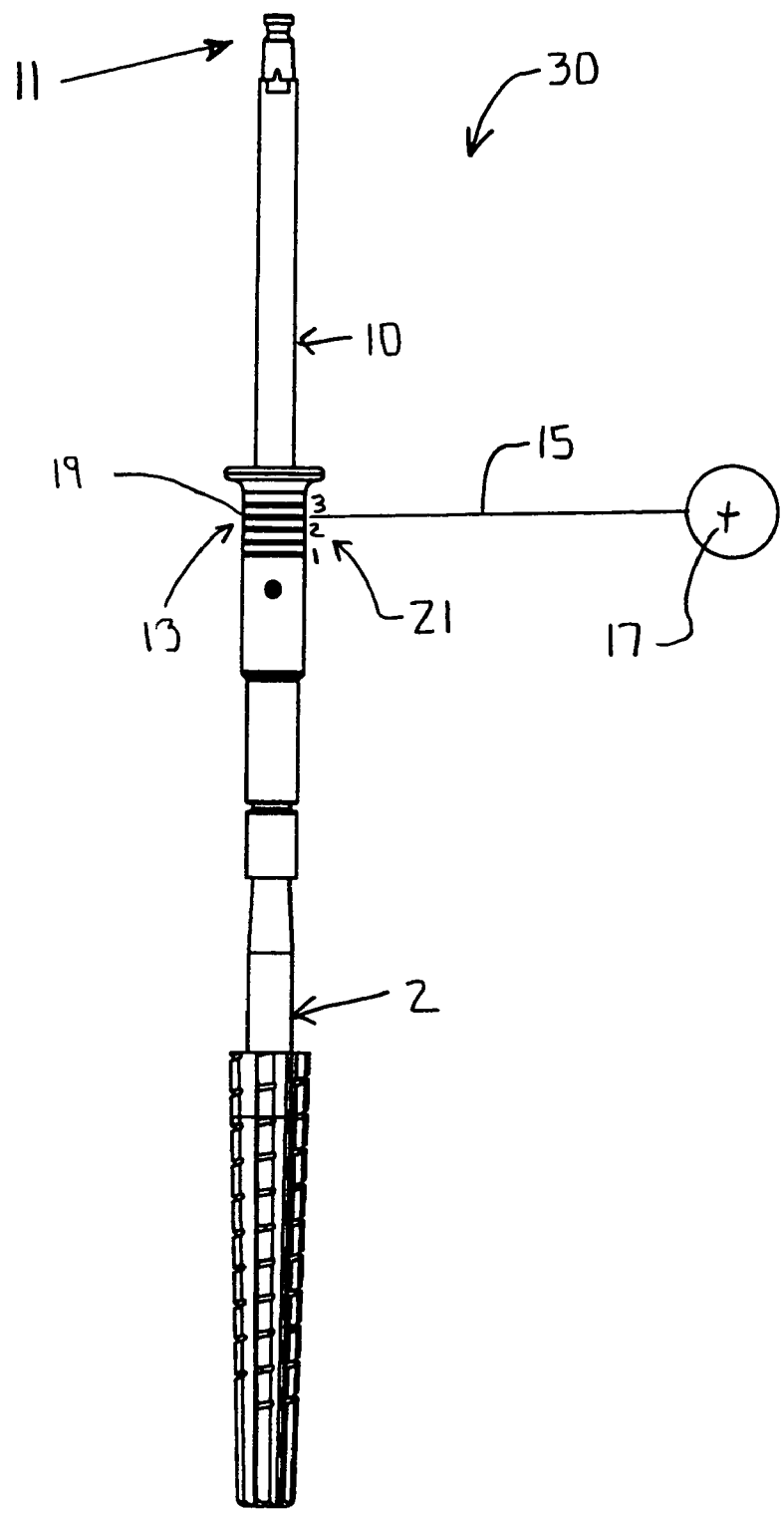
FIG. 3 is a plan view of the modular reamer assembly of FIG. 1.

Referring now to FIGS. 2 and 3, the reamer 2 is shown assembled onto the driver 10. The reamer and driver 10 form reamer driver assembly 30. The driver 10 includes a connector 11 for connecting to a driving device (not shown) that may be manual or powered.

Figure 4:
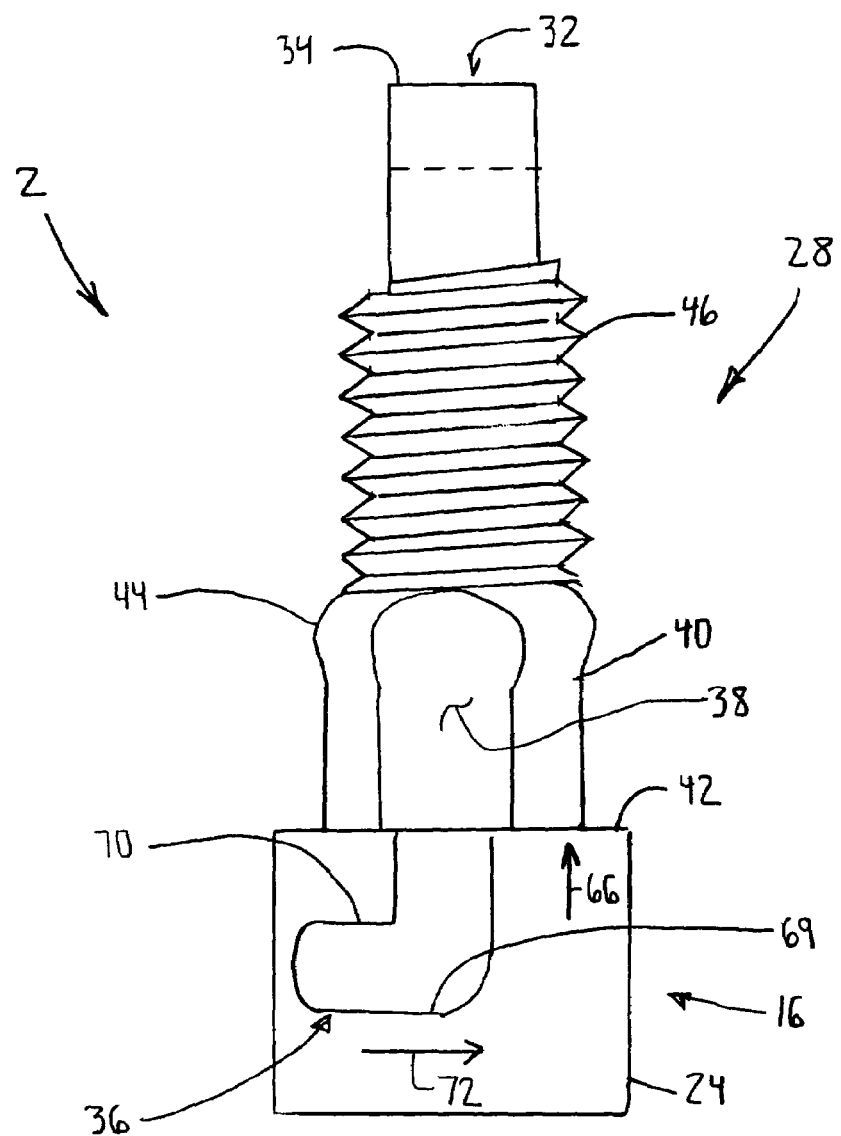
FIG. 4 is a partial plan view of the modular reamer assembly of FIG. 1 showing the proximal end in greater detail.

Referring now to FIG. 4, the locking feature 28 of the reamer 2 is shown in greater detail. The locking feature 28 may be any feature capable of cooperating with either the driver 10 or the trial 12. For example, and as shown in FIG. 4, the locking feature 28 may include a void in the form of an axial slot 32 extending axially from end 34 of the reamer 2.

As shown in FIG. 4, the locking feature 28 may further include a bayonet or J channel 36 formed in periphery 24 of the second portion 16 of the reamer 2. It should be appreciated that additional locking features or connecting features 28 may be provided. For example, as shown in FIG. 4, the locking feature 28 further includes opposed flats 38 formed on shank 40 extending from proximal end 42 of the second portion 16 of the reamer 2. The flats 38 are used primarily for alignment.

As shown in FIG. 4, the locking feature 28 may further include a ridge 44 extending from the shank 40. The locking feature 28 may further include external threads 46 extending outwardly from the ridge 44 of the shank 40.

Figure 5:
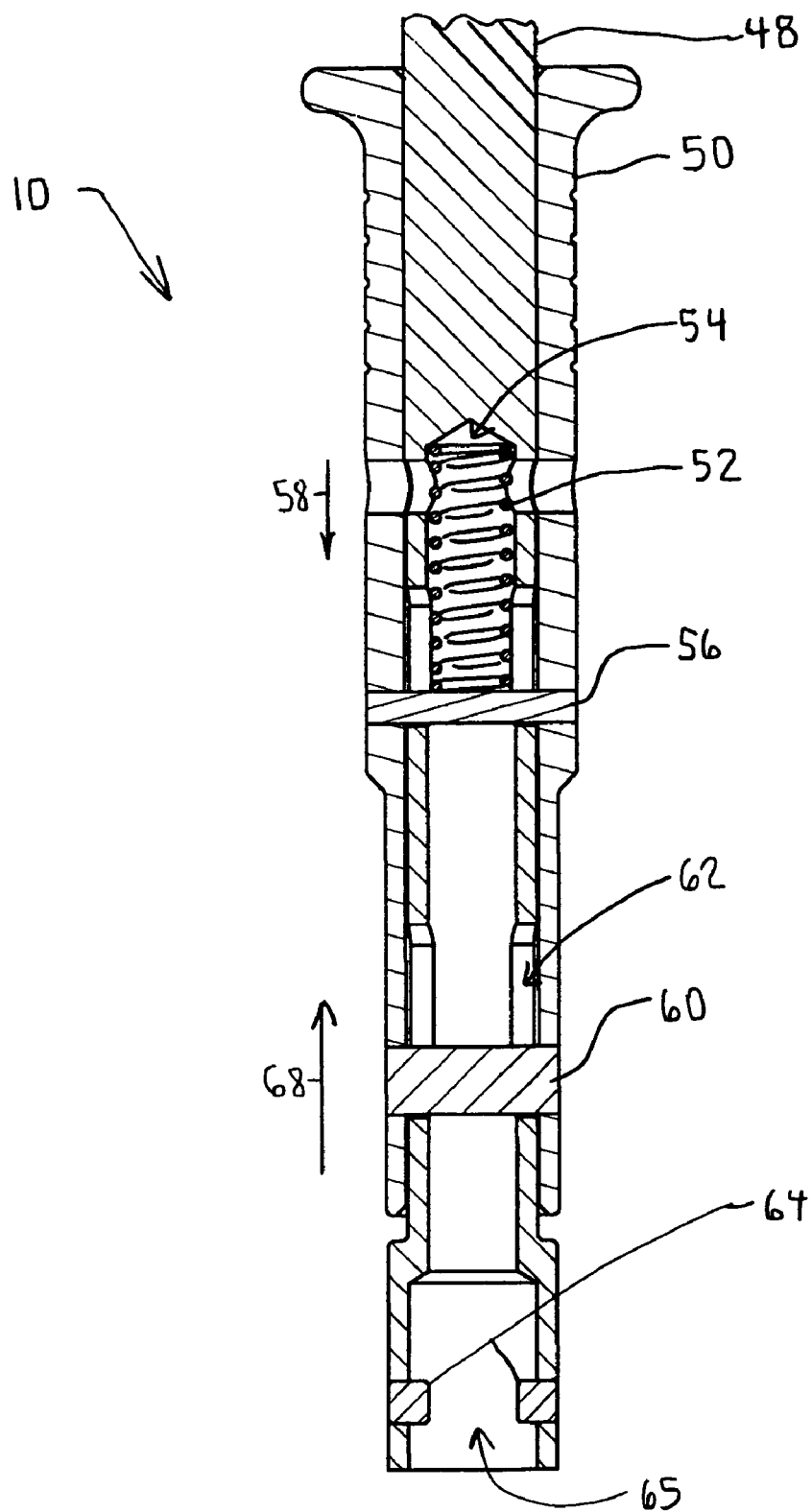
FIG. 5 is a partial cross sectional view of the modular reamer holder of the modular reamer assembly of FIG. 1.

Referring now to FIG. 5, the driver 10 is shown in greater detail. As shown in FIG. 5, the driver 10 includes a stem 48 to which a sleeve 50 is slidably fitted. A spring 52 is fitted in a central end opening 54 of the stem 48. Spring 52 is retained by spring retaining pin 56 operably connected to the sleeve 50. The spring 52 is utilized to urge the sleeve 50 in the direction of arrow 58 with respect to the stem 48.

A transverse cross-drive pin 60 is secured to the sleeve 50 and is contained within an elongated slot 62 in the stem 48. The drive pin 60 and the slot 62 serve to limit the relative motion of the sleeve 50 with respect to the stem 48. Internal pins 64 extend inwardly from hollow portion 65 of stem 48.

Referring now to FIG. 5 and FIG. 4, the reamer 2 is inserted into the driver 10 by aligning the periphery 24 of the second portion 16 of the reamer 2 into the hollow portion 65 of the stem 48. The internal pins 64 are aligned with the bayonet or J channel 36 and the reamer 2 is advanced in the direction of arrow 66.

By advancing the reamer 2 in the direction of arrow 66 the engagement of the end 34 of reamer 2 with the cross-drive pin 60 advances the cross-drive pin in the direction of arrow 68 until the spring 52 of the driver 10 is partially collapsed and the internal pins 64 contact distal surface 69 of the J-channel permitting the pins 64 to engage with second portion 70 of the bayonet or J-channel 36. The reamer 2 is thus rotated in the direction of arrow 72 until the cross-drive pin 60 is aligned with the axial slot 32 and the engagement is complete.

Figure 6:
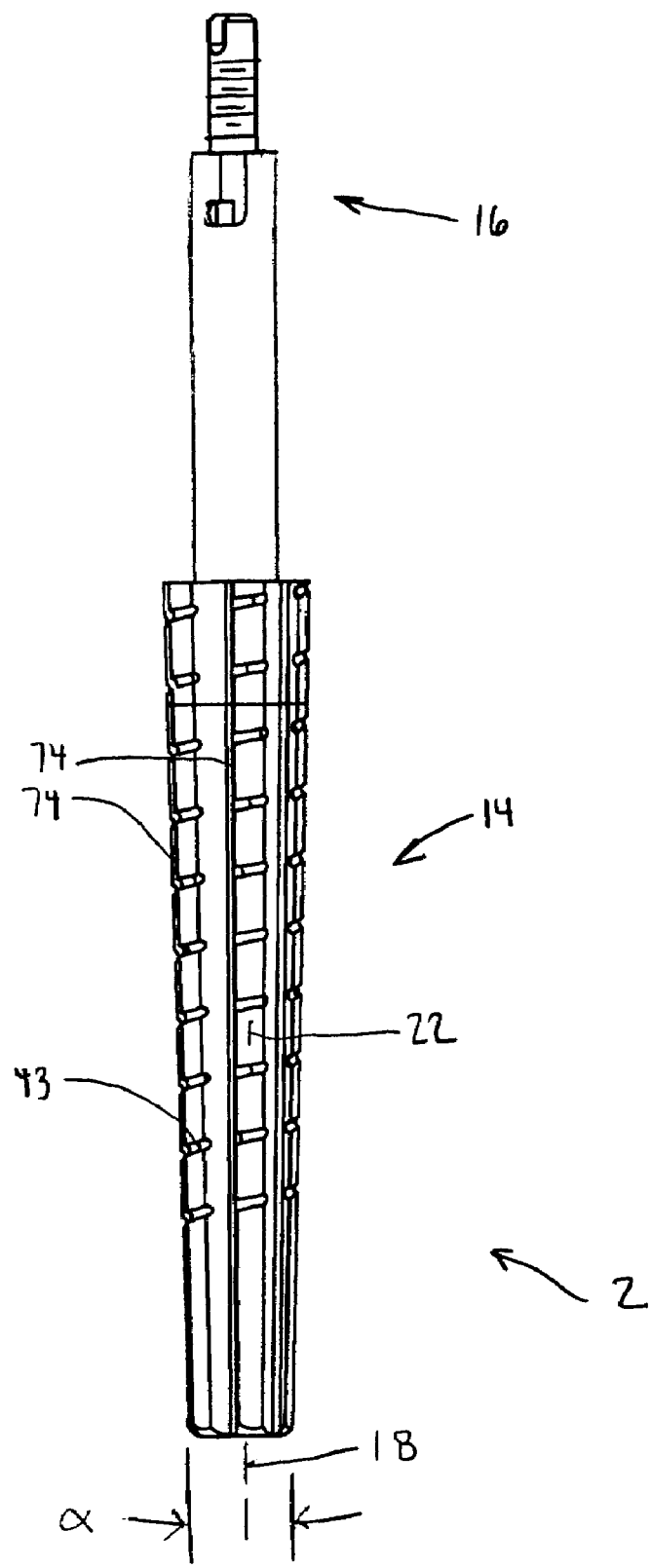
FIG. 6 is a plan view of the modular reamer of the reamer assembly of FIG. 1.

Referring now to FIG. 6, the first portion 14 of the reamer 2 is shown in greater detail. As shown in FIG. 6, the reamer 2 may have a tapered geometry. For example, the periphery 22 of the reamer 2 may form the included angle α. The angle α may be for example 0 to 20 degrees.

As shown in FIG. 6, the reamer 2 may include a plurality of flutes 74. The flutes 74 may extend in a straight axial direction as shown in FIG. 6. It should be appreciated that the flutes 74 may alternatively be spiraled or skewed with respect to the longitudinal axis 18 of the first portion 14. It should be appreciated that any number of flutes 74 may be utilized by the reamer 2.

Figure 7:
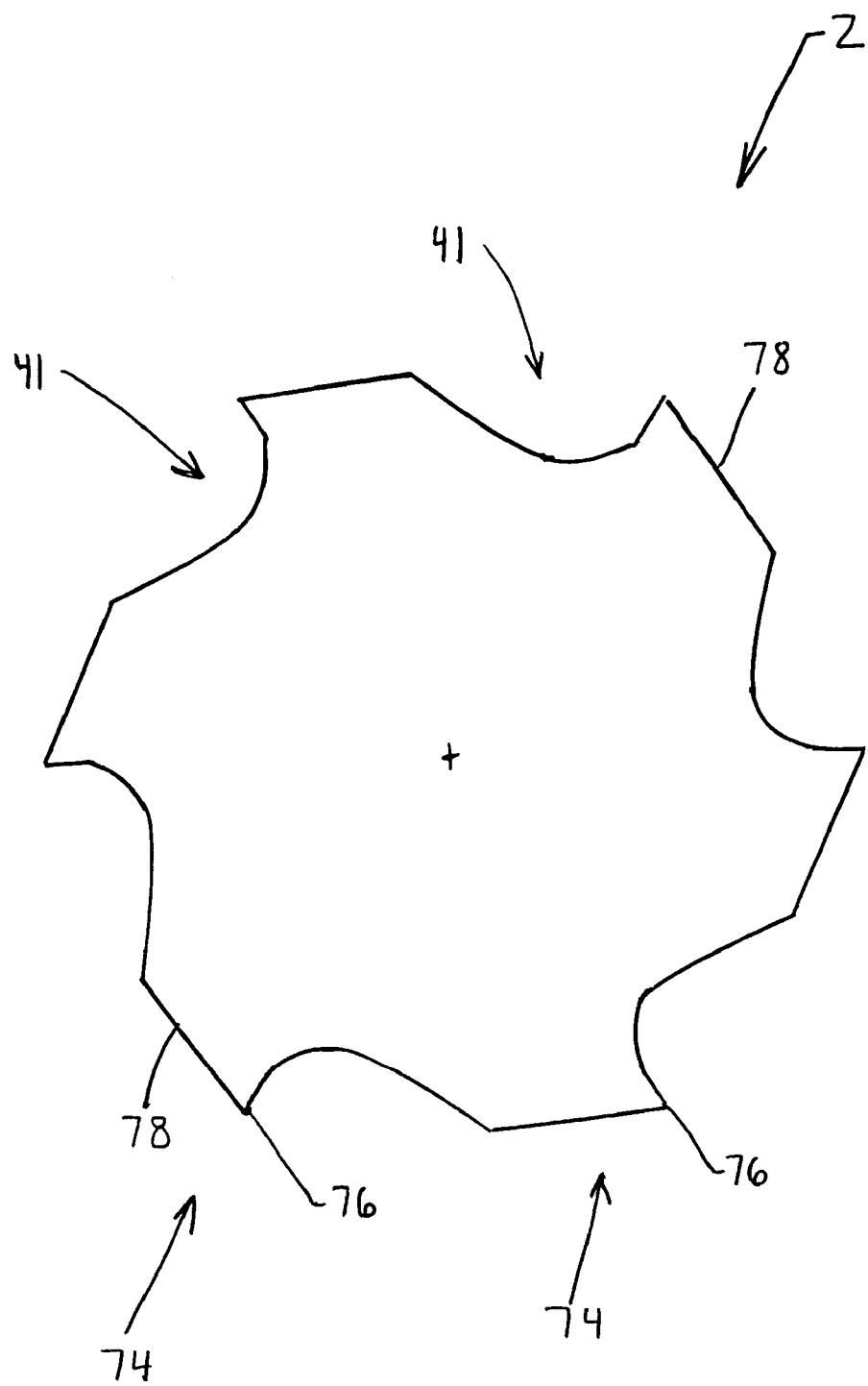
FIG. 7 is a bottom view of the modular reamer of FIG. 6.

As shown in FIGS. 6 and 7, the reamer 2 is shown with six (6) flutes. Each of the flutes 74 includes a cutting edge 76. A land 78 may be positioned close to the cutting edge 76 to stabilize the reamer 2 as it is cutting. Reliefs 41 may be positioned between adjacent lands 78. The reliefs 41 serve to provide a path for the removal and a location for collection of bone chips and other debris. As shown in FIG. 6, the reamer 2 may also include a plurality of grooves 43. The grooves 43 as shown in FIG. 6 may form a spiral pattern with respect to the first portion 14. The grooves 43 are used to help break up chips.

The reamer 2 may be made of any suitable durable material and may be made of, for example, a metal. The reamer is preferably made of a material that may be sterilized by a conventional sterilization technique such as by an autoclave. For example, the reamer 2 may be made of a cobalt chromium alloy, a stainless steel alloy, or any other durable metal or other cutting tool material. It should be appreciated that the reamer 2 may be integral or be made of multiple pieces or a modular construction.

The components of the driver 10 may be made of any suitable durable material and be made of, for example, a plastic or a metal. For example, if the driver 10 is made of a metal, it is preferably made of a sterilizable metal and may, for example, be made of a cobalt chromium alloy, a titanium alloy, or a stainless steel alloy. The driver 10 may also be made of any suitable durable steel which may be sterilized by standard methods, for example, by an autoclave.

Figure 8:
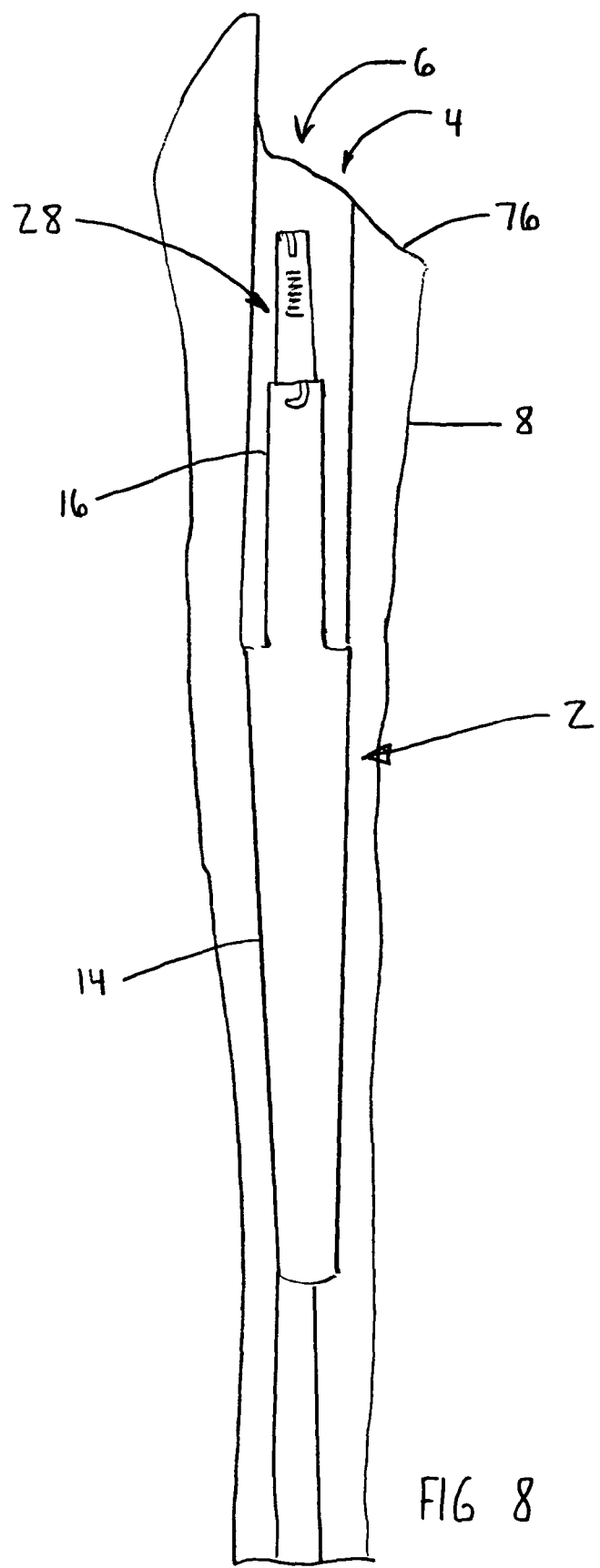
FIG. 8 is a plan view partially in cross-section of the modular reamer of FIG. 6 in position in the medullary canal of a femur.

Referring now to FIG. 8, the reamer 2 is shown in position on long bone or femur 8. The first portion 14 is shown in position in the canal 6 of cavity 4 of the femur 8. As shown in FIG. 8, the locking feature 28 and the proximal or second portion 16 may be positioned below the resection line 45.

Figure 9:
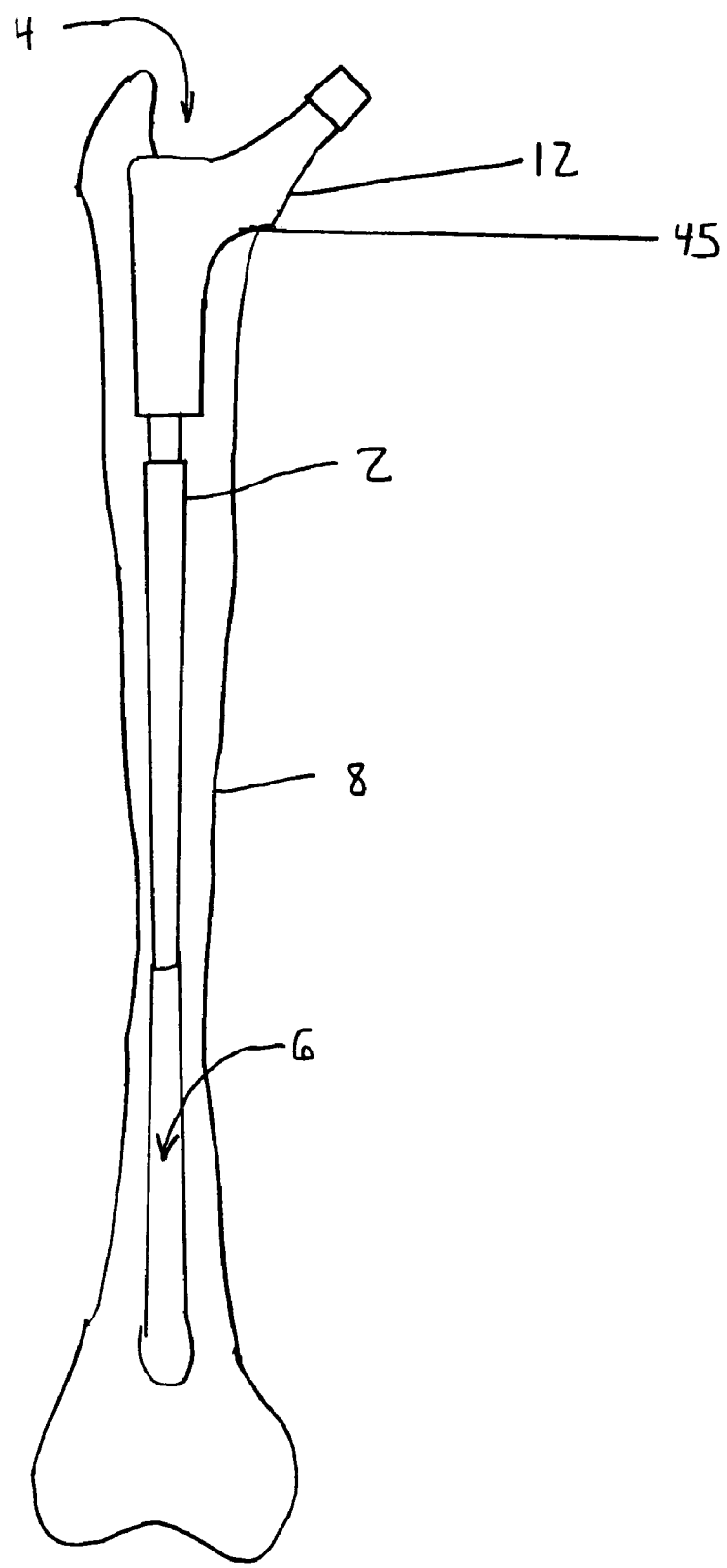
FIG. 9 is a plan view of a hip stem trail mounted on the modular reamer of FIG. 6 shown in position in the medullary canal of a femur prepared by the modular reamer assembly of FIG. 9.
Figure 1D:
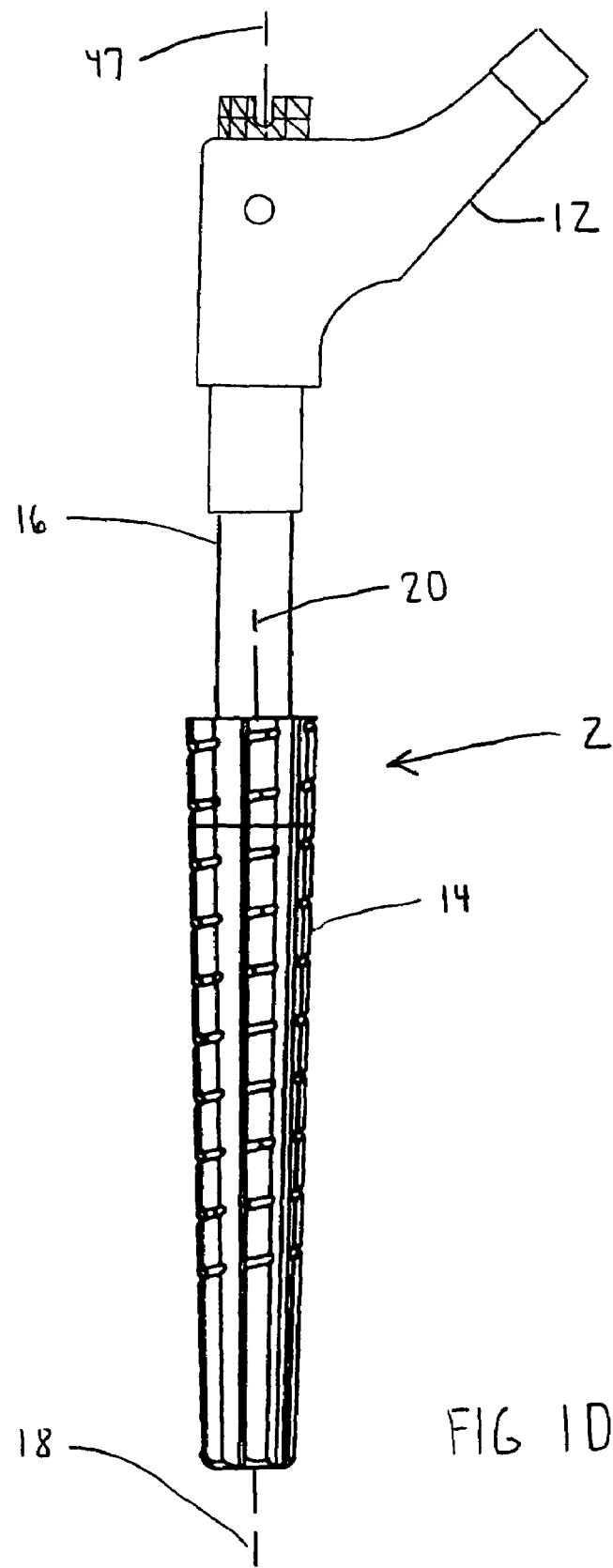

Referring now to FIG. 9, the trial 12 is shown installed on the reamer 2 while the reamer 2 is still in position in the cavity 4 of the canal 6 of the femur 8. Trial 12 is positioned in an anatomically correct position with respect to the resection line 45.

Referring now to FIG. 10, the trial 12 is shown in position assembled to reamer 2. The trial 12 is attached at second portion 16 of the reamer 2. As shown in FIG. 10, the trial 12 may have a trial longitudinal centerline 47 that is coincident with the centerline 20 of the second portion 16 of the reamer 2 as well as coincident with the centerline 18 of the first portion 14 of the reamer 2. It should be appreciated that any one of a series of proximal trials may be used with different dimensions such as offset height, calcar height etc.

Figure 11:
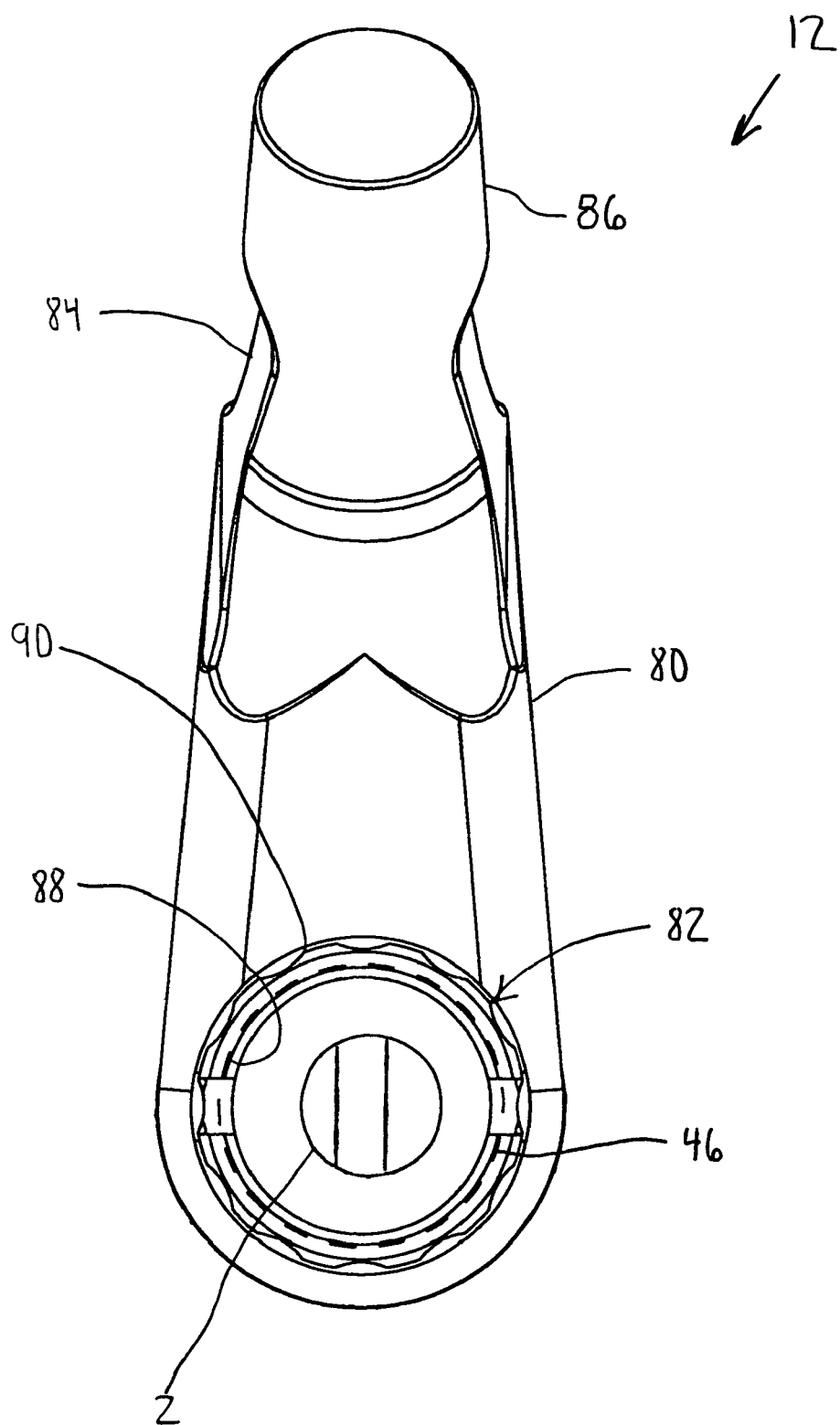
FIG. 11 is a top view of the hip stem trail and modular reamer assembly of FIG. 10.

Referring now to FIG. 11, the trial 12 is shown in greater detail. As shown in FIG. 11, the trial 12 includes a proximal body 80 and a nut 82 that is used to secure the proximal body 80 to the reamer 2. The proximal body 80 includes a neck 84 from which extends an external taper 86 for receiving the head (not shown) of the trial. The nut 82 is secured to the external threads 46 of the reamer 2 by internal threads 88 formed on the nut 82. A knurl 90 on the periphery of the nut 82 are used to provide additional grip to assist in securing the nut 82 to the reamer 2.

Figure 12:
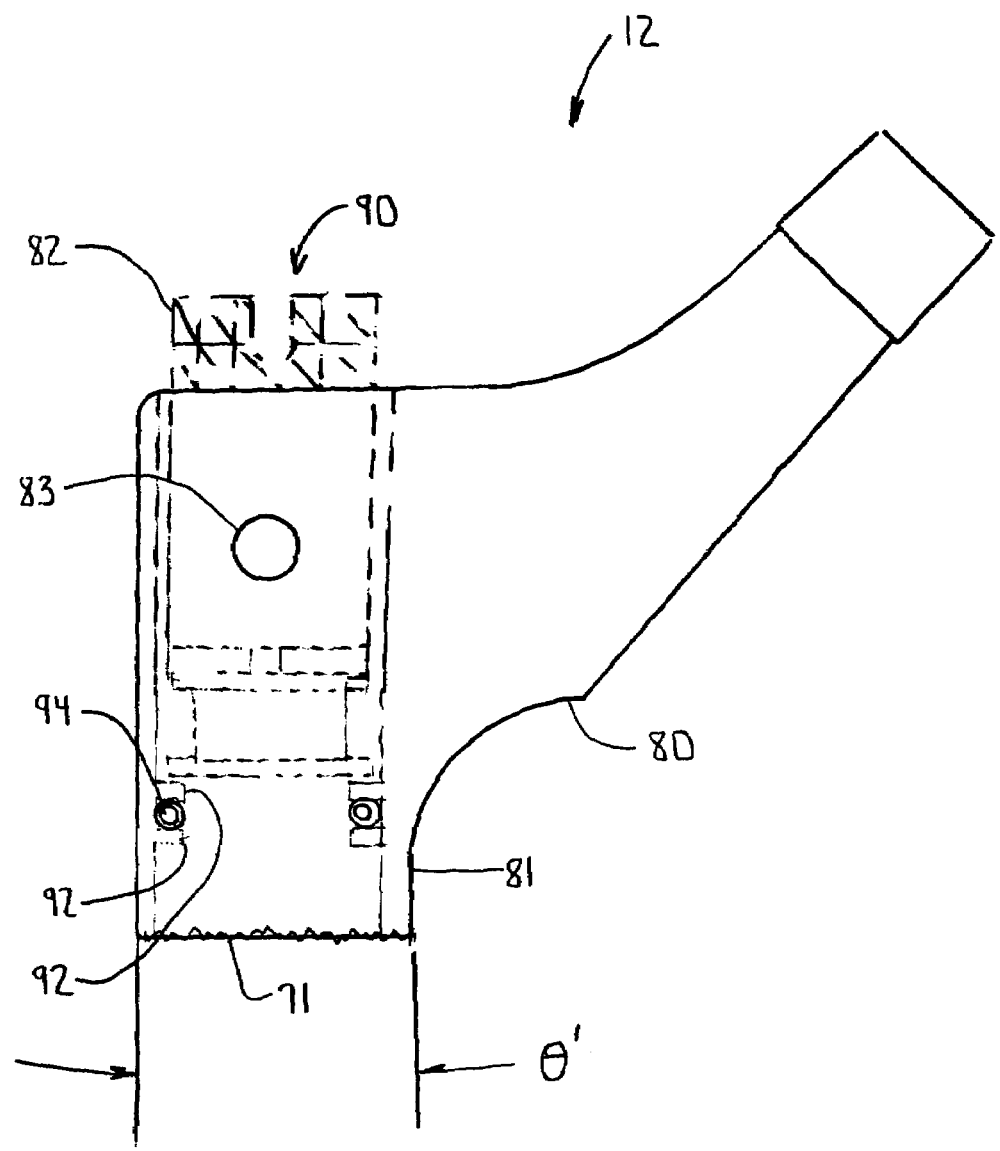
FIG. 12 is a plan view of the hip stem trail of the modular reamer assembly of FIG. 10.
Figure 13:
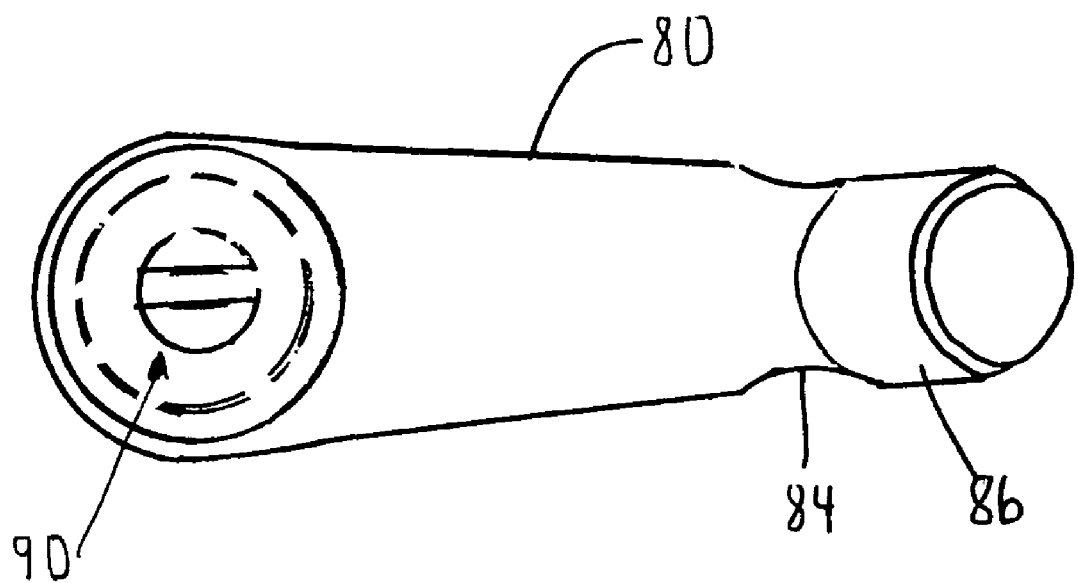
FIG. 13 is a top view of the hip stem trail of FIG. 12.

Referring now to FIGS. 12 and 13, the proximal body 80 is shown in greater detail. As shown in FIGS. 12 and 13, the body 80 defines a through opening 90 for receiving the nut 82. The through opening 90 and the body 80 define lips 92 for containing retaining spring 94. Retaining spring 94 cooperates with the ridge 44 of the head 40 of the reamer 2 (see FIG. 4) to provide a connecting feature for snapping the body 80 into position on the reamer 2.

Referring now to FIGS. 14 and 15, the nut 82 is shown in greater detail. Axial slots 96 extend inwardly from end 97 of the nut 82. The slots 96 serve to provide a drive feature for properly torquing the nut 82 to the reamer 2. The nut 82 has an outer periphery 98 which is matingly fitted with the through opening 90 to permit the nut 82 to fit within the opening 90 of body 80 of trial 12 (see FIG. 12). A recess 93 is formed in the outer periphery 98 of the nut 82. Retaining pins 99 (shown in phantom) extending axially from the body 80 into the opening 90 of body 80 of trial 12 (see FIG. 12) engage in the recess 93 to restrain the nut 82 within the opening 90 of the body 80.

Figure 16:
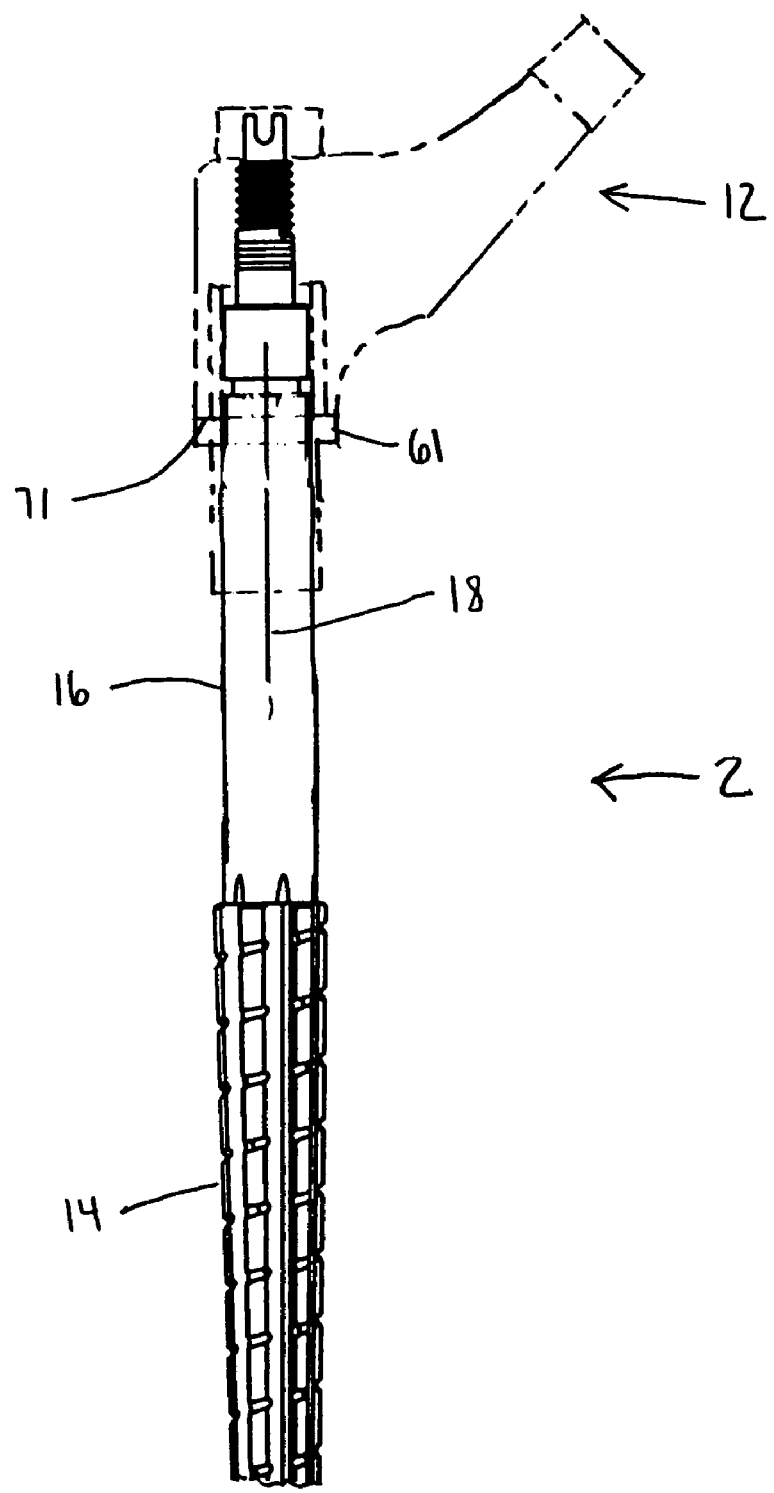
FIG. 16 is a plan view of the modular reamer of FIG. 6 with the hip stem trial of FIG. 12 shown in phantom.

Referring now to FIG. 16, the trial 12 is shown installed on the reamer 2. It should be appreciated that the trial 12 and the reamer 2 may be designed such that the trial 12 and the reamer 2 directly connect to each other. As shown in FIG. 16, a reamer trial adapter 61 may be positioned between the reamer 2 and the trial 12. The use of a reamer trial adapter 61 permits greater flexibility in the design of the trial 12 and in the design of the reamer 2, so that the reamer 2 may be suitably connected to an optimally designed driver such as driver 10 of FIG. 5, and such that the trial 12 may be properly designed to cooperate with reamer 2.

Figure 17:
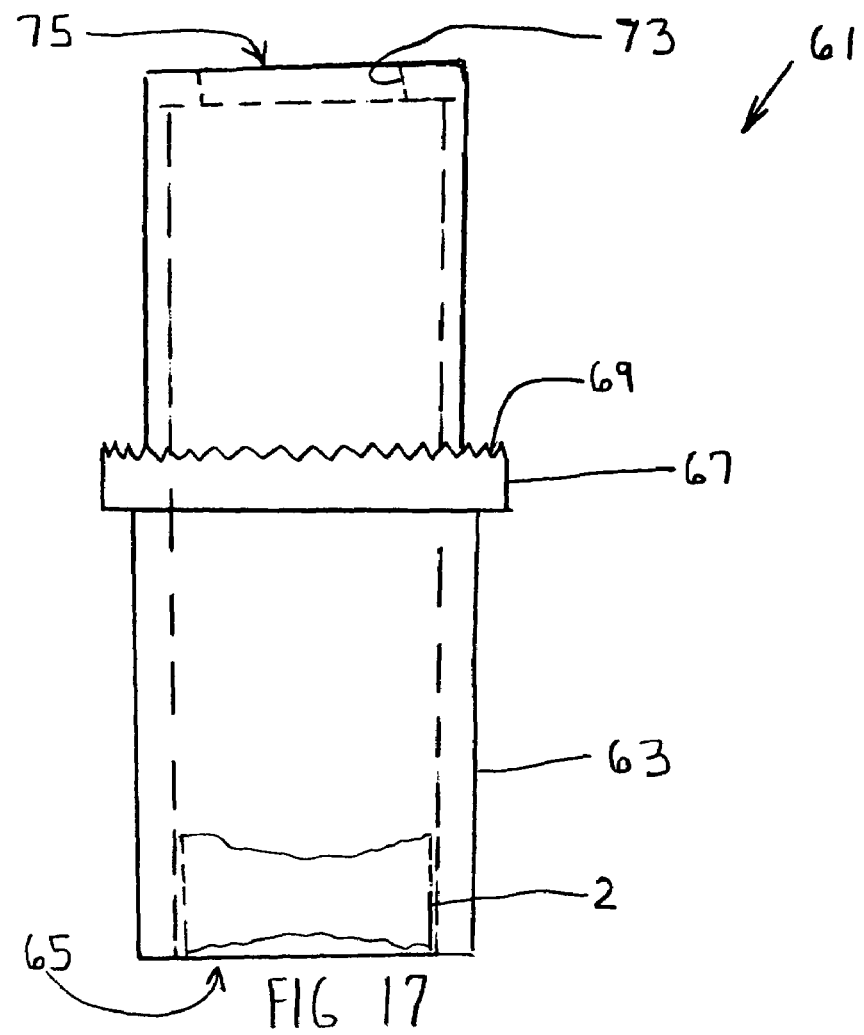
FIG. 17 is a plan view of an adaptor for use with the modular reamer of FIG. 6 and with the hip stem trial of FIG. 12.
Figure 18:
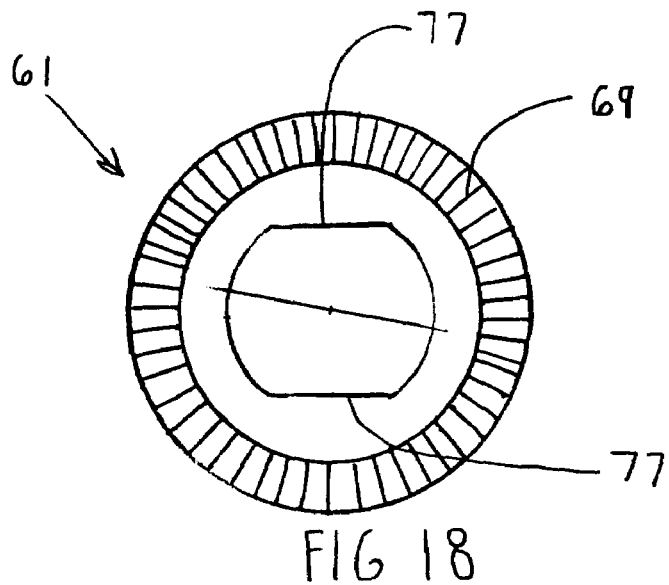
FIG. 18 is a top view of the adaptor of FIG. 17.

Referring now FIGS. 17 and 18, the reamer trial adapter 61 is shown in greater detail. The reamer trial adapter 61 has a generally hollow cylindrical body 63. The reamer trial adapter 61 may be pinned to the proximal trial 12 by pins (not shown). A central opening 65 is formed in the hollow body 63 and the central opening 65 is designed to receive the second portion of the reamer 2. A flange 67 is centrally positioned and extends outwardly from the body 63. Radial teeth 69 are positioned on a surface of the flange 67. The radial teeth 69 mate with radial teeth 71 located on the trial 12. (See FIG. 16).

An end cap 73 is positioned on one end of the body 63 and defines an end cap opening 75 therein. The end cap 73 defines parallel spaced apart flats 77. Flats 77 on the adapter 61 are matingly fitted to receive the flats 38 of the shank 40 of the reamer 2 (see FIG. 4).

Figure 19:
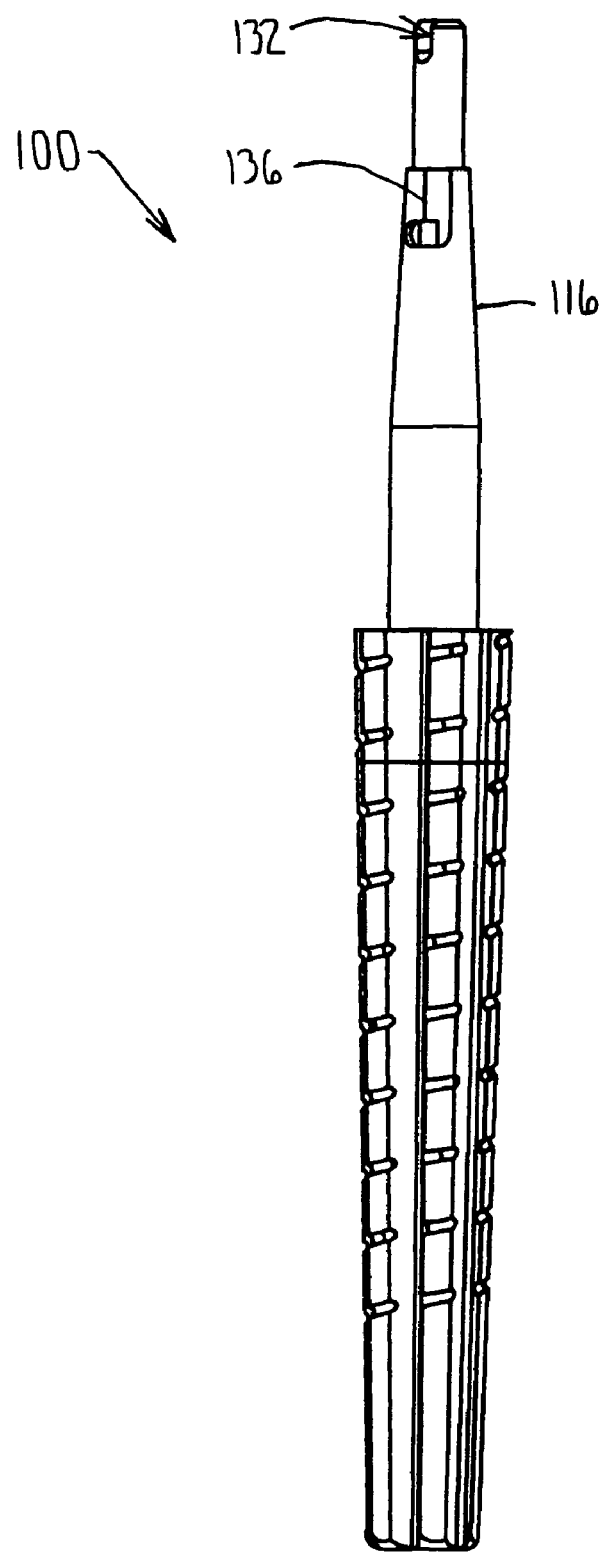
FIG. 19 is a plan view of another embodiment of a modular reamer according to the present invention with a tapered shank and without a threaded proximal end.

Another embodiment of the reamer 2 of the present invention is shown in FIG. 19 as reamer 100. The reamer 100 of FIG. 19 is similar to the reamer 2 of FIG. 6 except that the reamer 100 includes a second portion 116 that is tapered. The second portion 116 may include a bayonet or J-channel 136 similar to the bayonet or J-channel 36 of the reamer 10 and may include a slot 132 similar to the slot 32 of the reamer 2 of FIG. 6. Reamer 100 of FIG. 19 does not include the external threads as the tapered second portion 116 may be utilized with a mating taper on the corresponding trial to secure the trial to the reamer 100.

Figure 20:
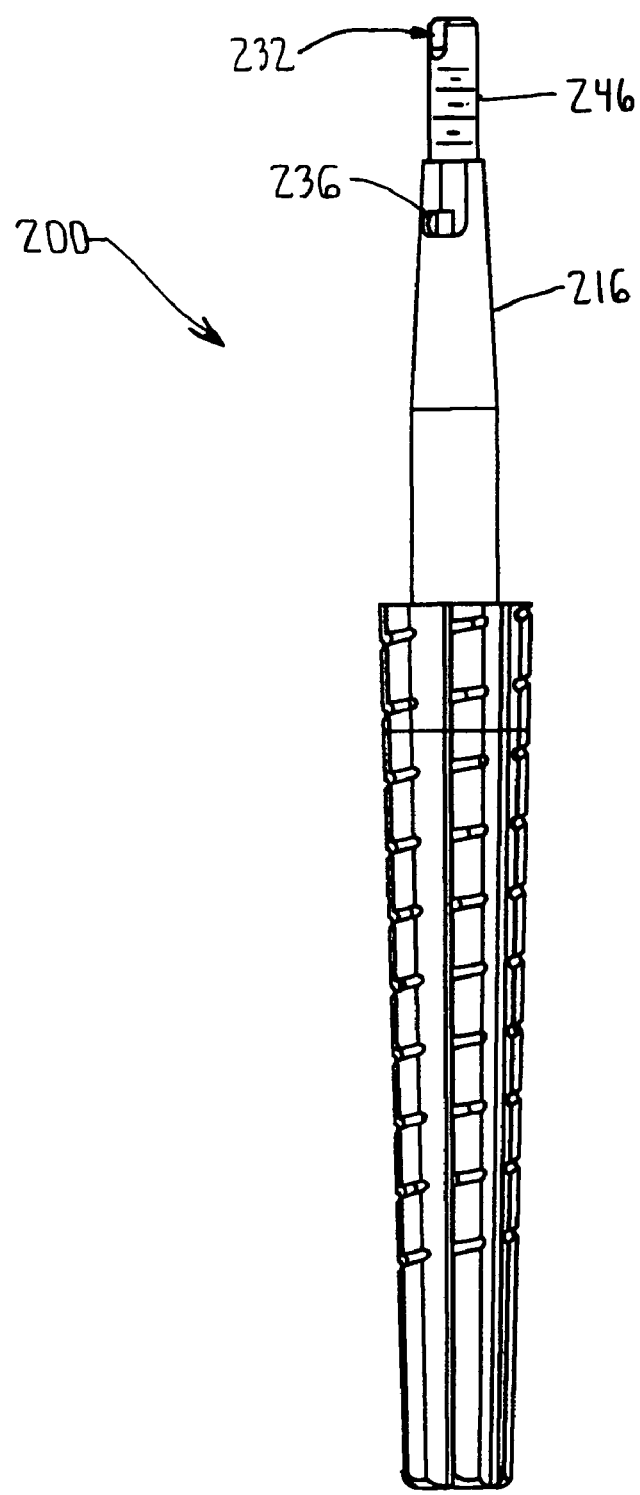
FIG. 20 is a plan view of another embodiment of a modular reamer according to the present invention with a tapered shank and with a threaded proximal end.

Referring now to FIG. 20, another embodiment of the reamer of the present invention is shown as reamer 200. Reamer 200 is similar to reamer 100 of FIG. 19 and includes a second portion 216 that is tapered similar to that of second portion 116 of the reamer 100 of FIG. 19. The reamer 200 of FIG. 20 includes external threads 246 similar to the threads 46 of the reamer 10. The threads 246 mate with threads (not shown) on the corresponding trial (not shown). The reamer 200 of FIG. 20 may similarly use the bayonet or J-channel 236 and a slot 232 for securement to the corresponding driver (not shown).

Figure 21:
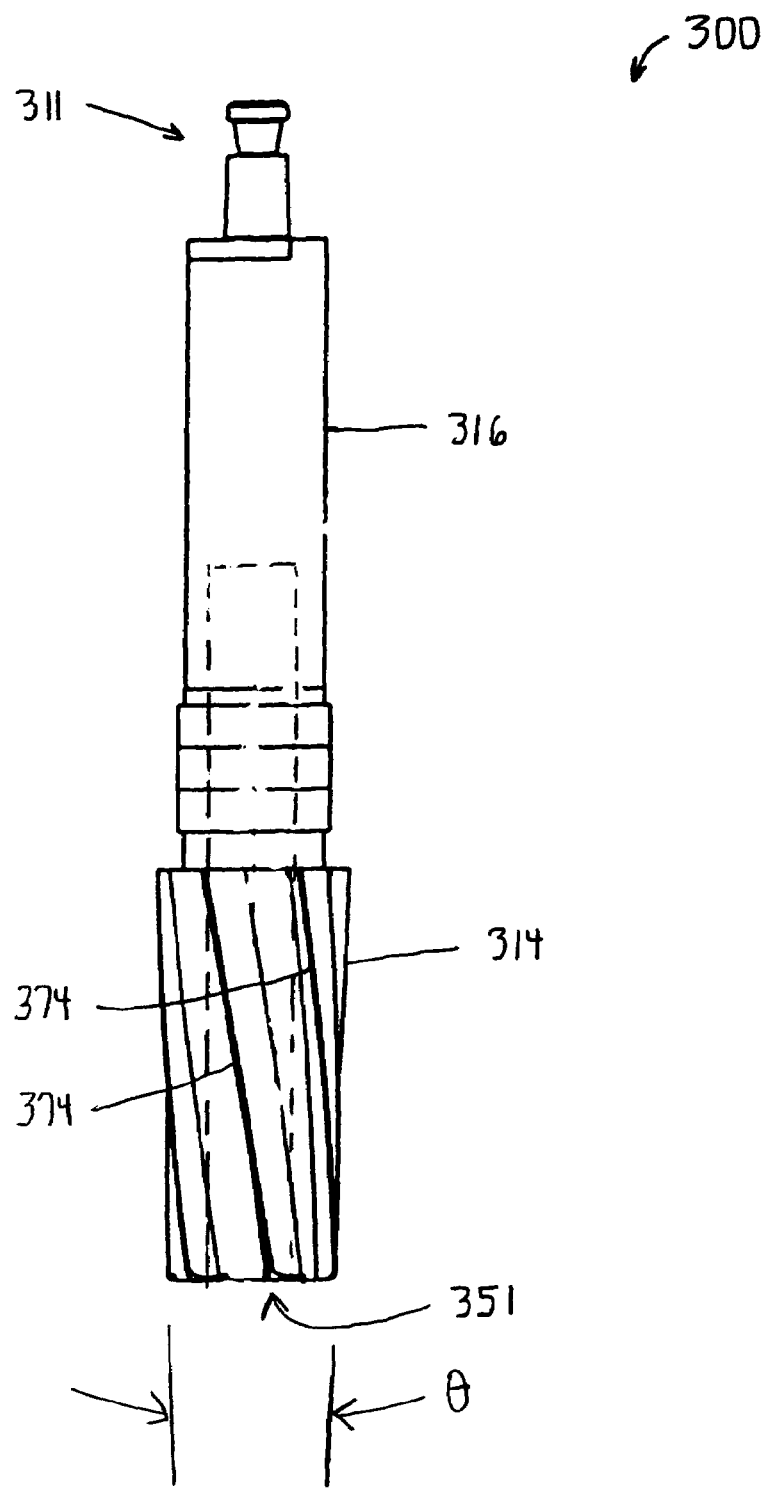
FIG. 21 is a plan view of a proximal reamer for use with the modular reamer of FIG. 6 to provide clearance for the hip stem trial of FIG. 12.

Referring now to FIG. 21, another embodiment of the present invention is shown as reamer 300. The reamer 300 is utilized to provide clearance for the tapered cylindrical periphery 81 of the body 80 of the trial 12 (see FIG. 12). Reamer 300 includes a shank portion 316 and a cutting tooth portion 314. Cutting tooth portion 314 includes a plurality of spaced apart flutes 374.

As shown in FIG. 21, the flutes 374 may have a spiral orientation. The cutting tooth portion 314 forms an included angle θ that may be similar to the included angle θ' formed by the tapered cylindrical periphery 81 of the body 80 of the trial 12 (see FIG. 12).

The reamer 300 includes a connector 311 extending outwardly from the shank portion 314 of the reamer 300. The connector 311 is similar to the connector 11 of the driver 10 (see FIG. 3). The reamer 300 includes a central cavity 351 formed in the cutting tooth portion 314 of the reamer 300. The central cavity 351 is sized for rotatably receiving the second portion 16 of the reamer 2 (see FIG. 6).

After the reamer 2 has been utilized to prepare the cavity 4 in the canal 6 and the reamer 2 is left in position in the femur 8 (see FIG. 8), the reamer 300 is positioned over the reamer 2 with the center cavity 351 fitting over the second portion 16 of the reamer 2. The reamer 300 is then rotated to remove additional material in the proximal portion of the femur 8 for permitting the receiving of the body 80 of the trial 12 (see FIG. 12).

Figure 22:
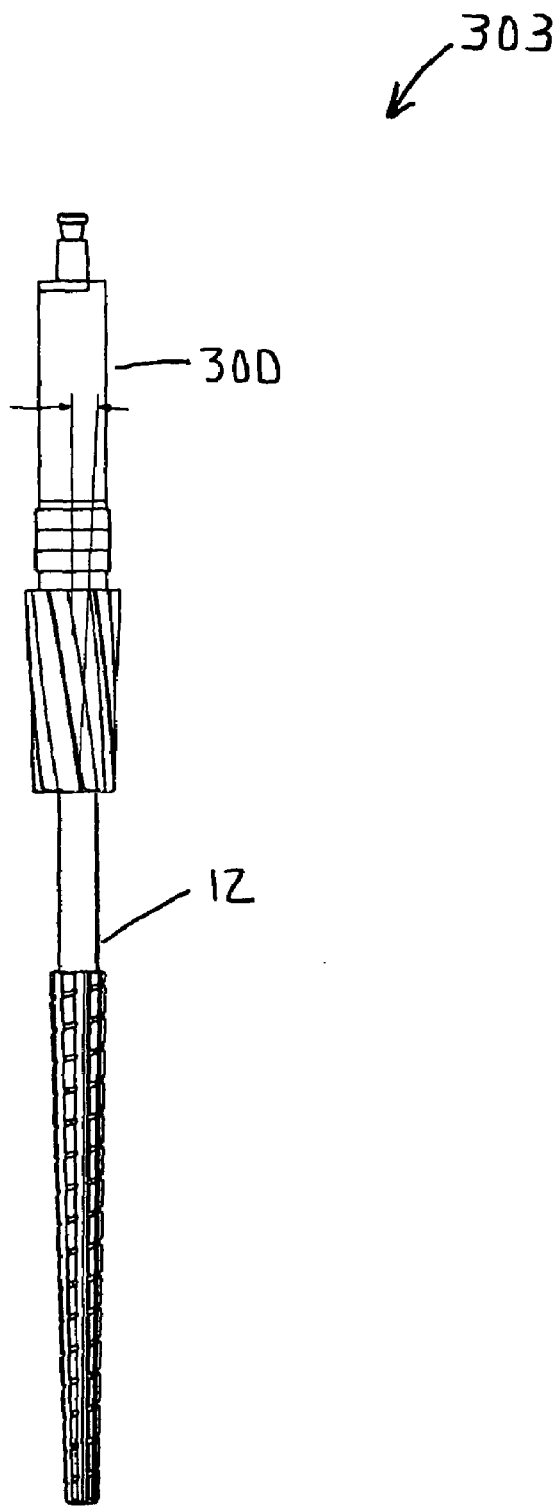
FIG. 22 is a plan view of a proximal reamer of FIG. 21 shown in position on the modular reamer of FIG. 6.

Referring now to FIG. 22, reamer assembly 303 is shown. Reamer assembly 303 includes the reamer 300 in position over the reamer 12.

Figure 23:
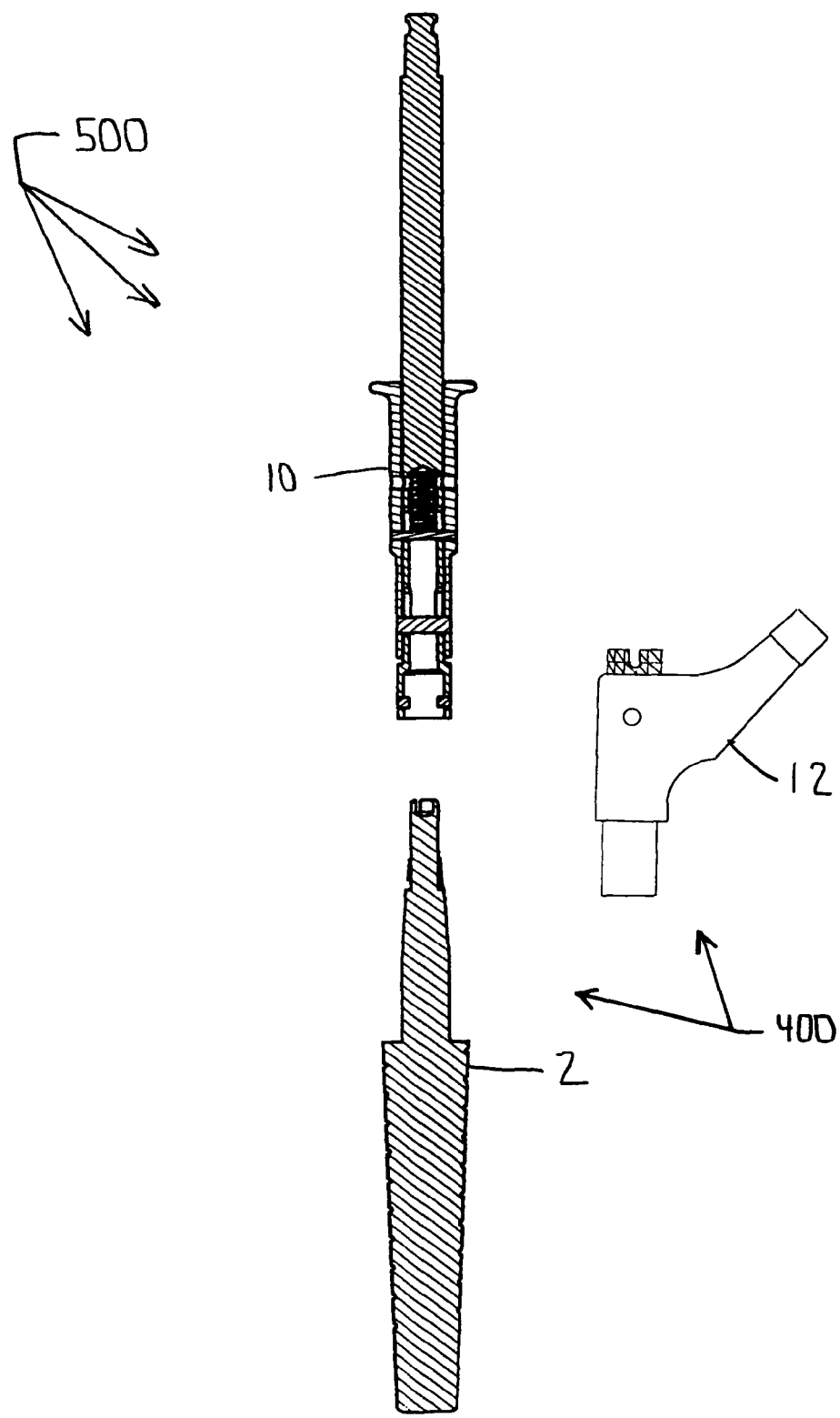
FIG. 23 is a cross sectional exploded view of the modular reamer assembly of FIG. 1 and a plan view of the trial of FIG. 12.

Referring now to FIG. 23, an alternate embodiment of the present invention is shown as kit 400. The kit 400 includes the reamer 2 and the trial 12. It should be appreciated that reamer 2 and the trial 12 may be separately packaged or that the reamer 2 and the trial 12 may be packaged together. It should also be appreciated that the kit 400 may include a series of reamers and a series of trials and proximal reamers, so that all commonly used sizes are available for the surgeon.

Continuing to refer to FIG. 23, another embodiment of the present invention is shown as kit 500. Kit 500 includes the reamer 2, the driver 10 and the trial 12. It should be appreciated that the driver 10, the reamer 2 and the trial 12 may each be individually packaged or that the trial 12, the driver 10 and the reamer 2 may be packaged together in a common container.

Figure 24:
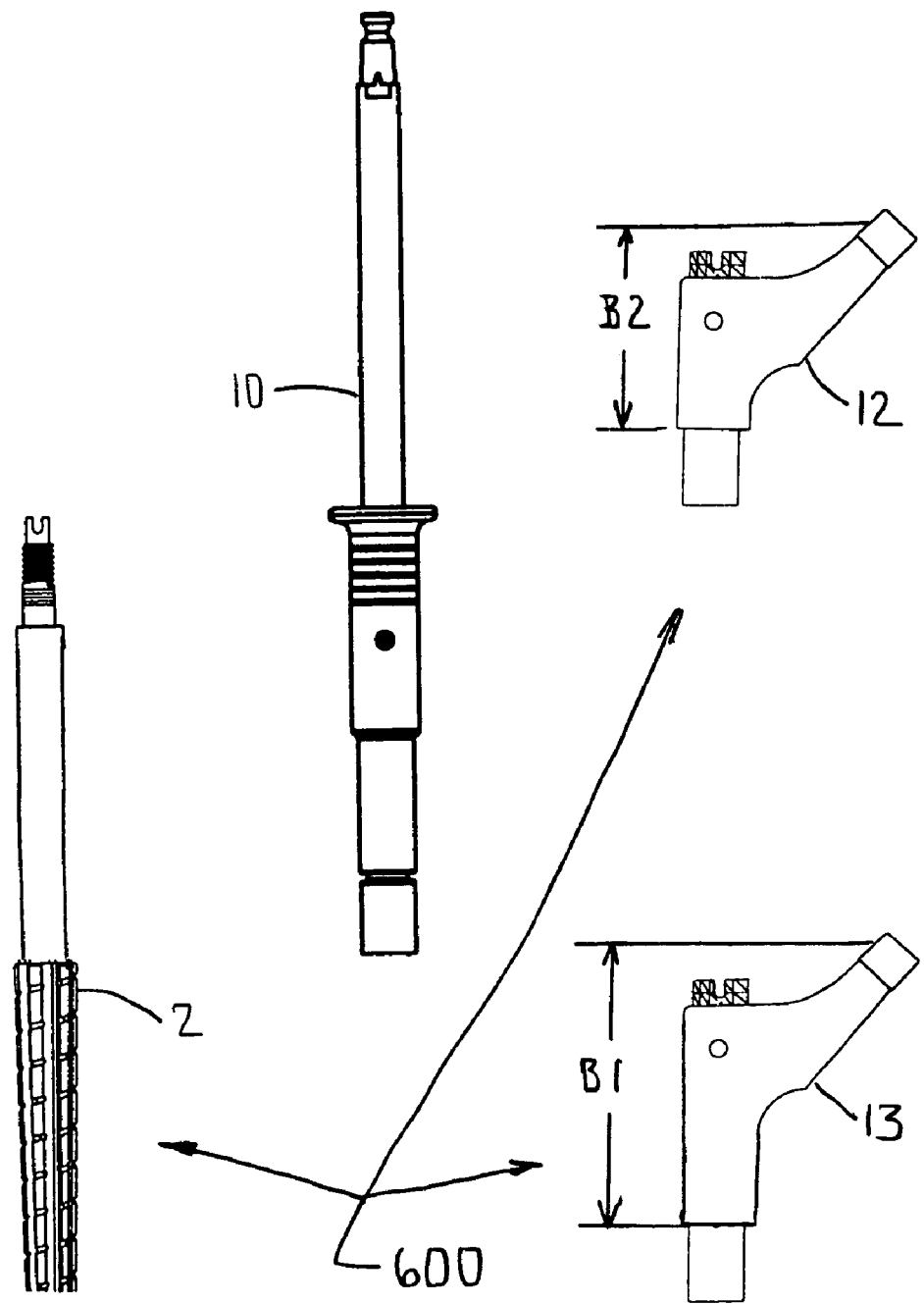
FIG. 24 is a plan view of another embodiment of the present invention in the form of a kit including the modular reamer of FIG. 6, the driver of FIG. 6, the hip stem trial of FIG. 12, the proximal reamer of FIG. 21, and an additional trial.

Referring now to FIG. 24, another embodiment of the present invention is shown as kit 600. Kit 600 includes the reamer 2 and the first trial 12. The kit 600 further includes a second trial 13. The second trial 13 has at least one dimension different than that of the first trial 12. For example, the first trial has a calcar height B2 which is significantly less than the calcar height B1 of the second trial 13. It should be appreciated that the reamer 2, the first trial 12 and the second trial 13 may each be individually packaged or the reamer 2, the first trial 12 and the second trial 13 may all be packaged in a common container.

When performing an arthroplasty, for example a total hip arthroplasty, the trial 12 is subjected to a trial reduction. In the trial reduction procedure, the trial is positioned in the orthopaedic joint and the limb, for example the leg, is moved about in the normal operating limits to assure to the surgeon that the correct trial has been selected and that the trial is properly positioned. After the trial reduction is performed, the position of the trial 12 relative to the femur 8 is recorded by the surgeon. The position of the implant to be positioned later is preferably in the same corresponding location.

The surgeon may utilize any of a number of techniques to provide for the prosthesis to be in the same location to that of the trial. For example, the surgeon may merely physically note the position of the trial and correspondingly position the prosthesis. Alternatively, a mark or indicia may be placed on the patient to indicate the proper orientation of the prosthesis. Alternatively, instruments may be provided which record the position of the trial and which instruments are utilized to properly position the implant based on the position of the trial. The surgeon also use indicia in the form of witness marks on the drive shaft that correspond with head centers.

To assist the surgeon as shown in FIG. 3, the driver 10 may include indicia 13 formed on the driver 10. The indicia 13 may be used to assist in determining the proper depth of the distal reamer 2 during the reaming operation. The indicia 13 will preferably be used in conjunction with a visual line 15 with, for example, a bony landmark on the patient, for example, head centerline 17. The surgeon aligns the head centerline 17 with the indicia 13 to determine the proper depth of the reamer 2. The indicia 13 may be in the form of marks or lines 19. Numbers or letters 21 may be placed adjacent the lines 19 to refer to a particular trial or prosthesis which should be used when the line 19 corresponds to the visualization line 15.

Figure 25:
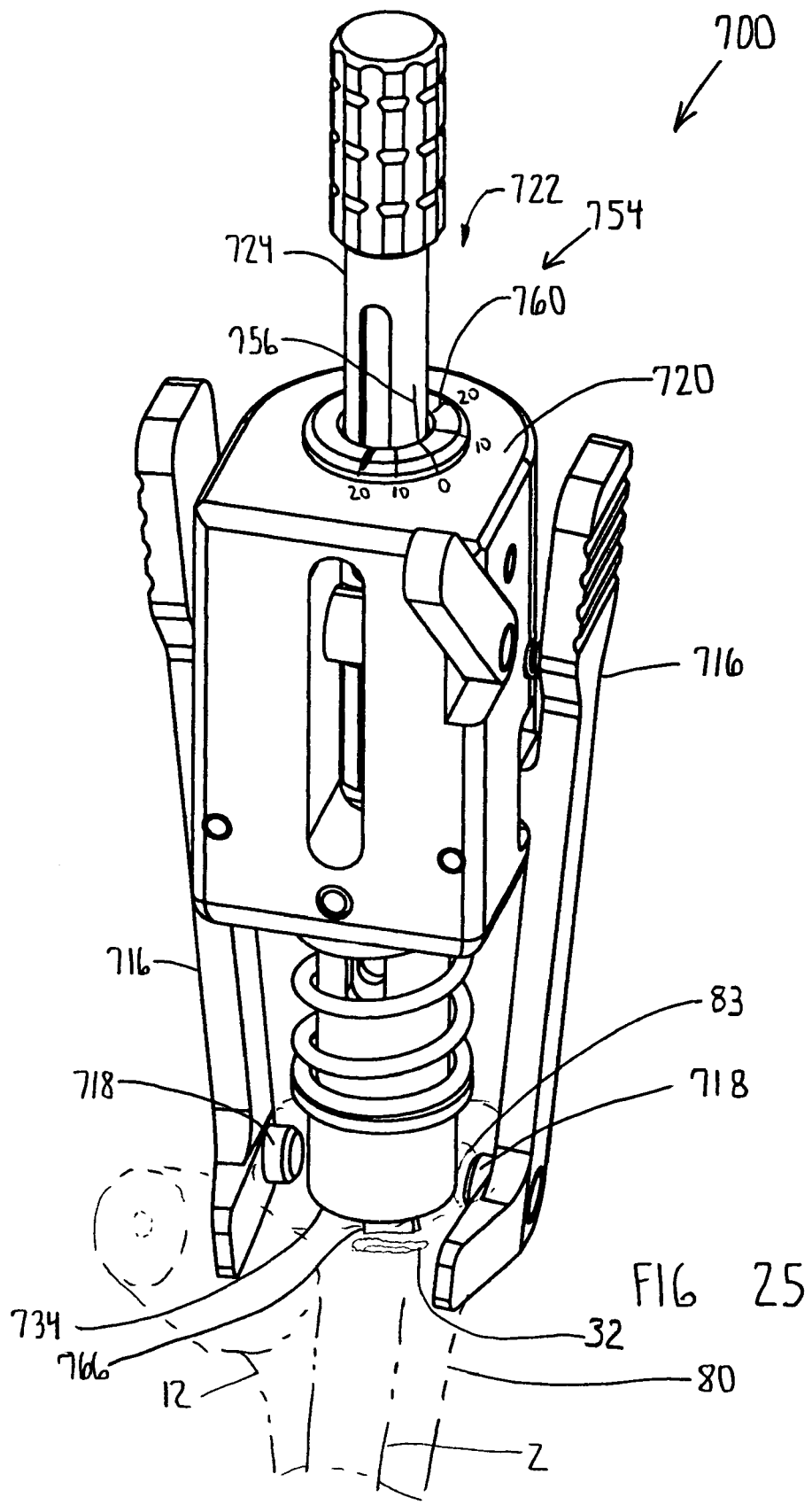
FIG. 25 is a perspective view of an alignment tool for use in aligning the components of an implant to correspond to those of the hip stem trail with the proximal portion of the hip stem trail and modular reamer assembly of FIG. 8 shown in phantom.

Referring now to FIG. 25, one such instrument is shown as alignment device 700. As shown in FIG. 25, the alignment device 700 includes body 720 that has a longitudinal opening 722. The longitudinal opening 722 receives a rod 724 therein. The rod 724 includes a tang 766 extending from an end 734 of the rod 724. The tang 766 matingly engages slot 32 of the reamer 2.

Arms 716 are pivotally connected to the body 720. The arms 716 include pins 718 which matingly engage openings 83 in the body 80 of the trial 12. The relative position of the slot 32 to the openings 83 is transferred into the alignment device by means of the relative position of the pins 718 to the tang 766. The relative position of the pins 718 to the tang 766 may be observed by indicia 754 in the form of, for example, lines 760 on the body 720 which are aligned with lines 756 on the rod 724. The alignment device 700 may then later be used to orient the proximal and distal components of the prosthesis.

Referring now to FIGS. 26, 27, 28, 29 and 30, a prosthesis 815 is shown for use with the reamer of the present invention. The prosthesis 815 includes a proximal body 817 and a distal stem 819. The proximal body includes a pair of spaced apart orientation holes 821.

Figure 27:
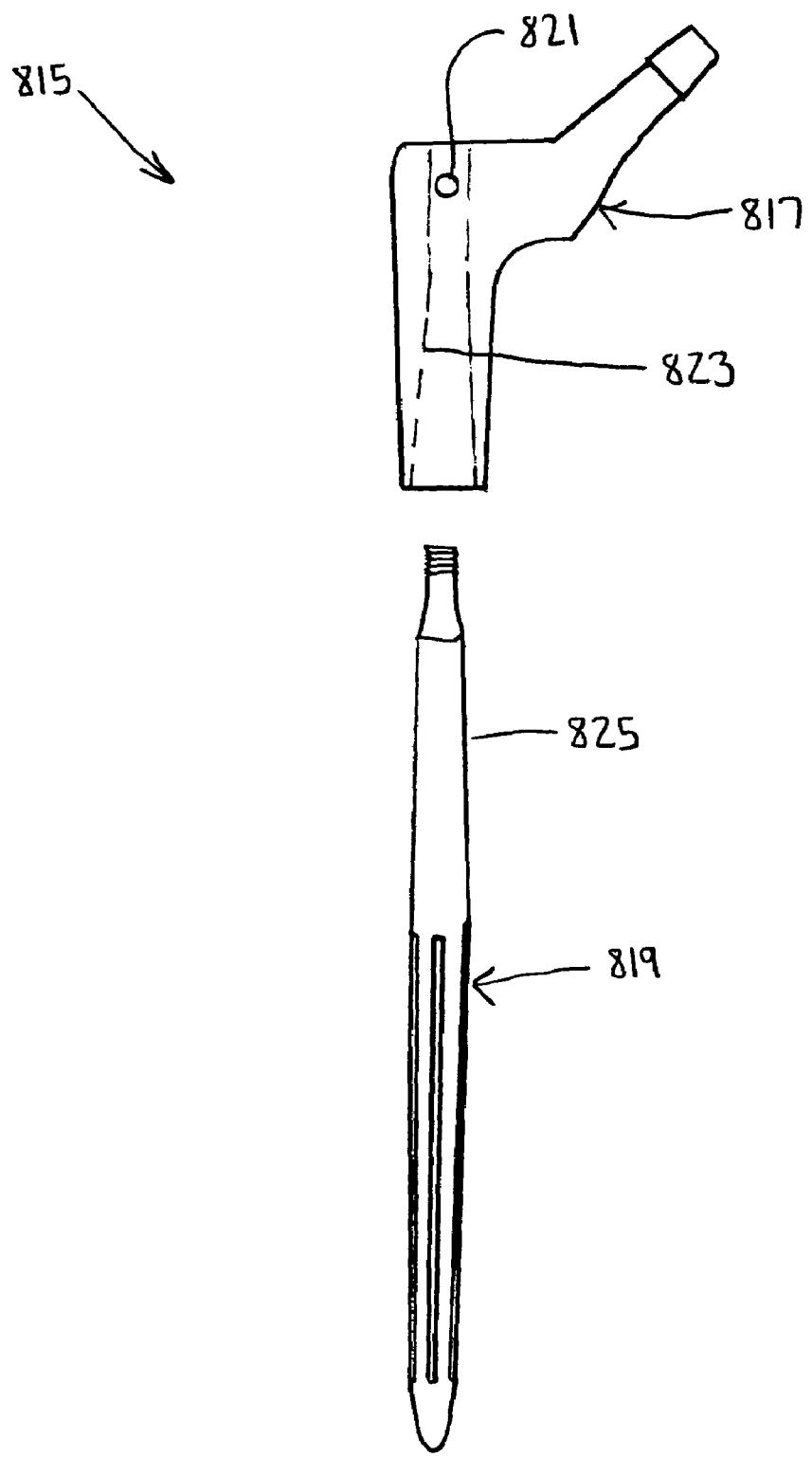
FIG. 27 is an exploded plan view of the modular hip stem of FIG. 26.

Referring now to FIG. 27, the proximal body 817 of the prosthesis 815 includes an internal taper 823 that is matingly fitted to external taper 825 of the distal stem 819.

Figure 28:
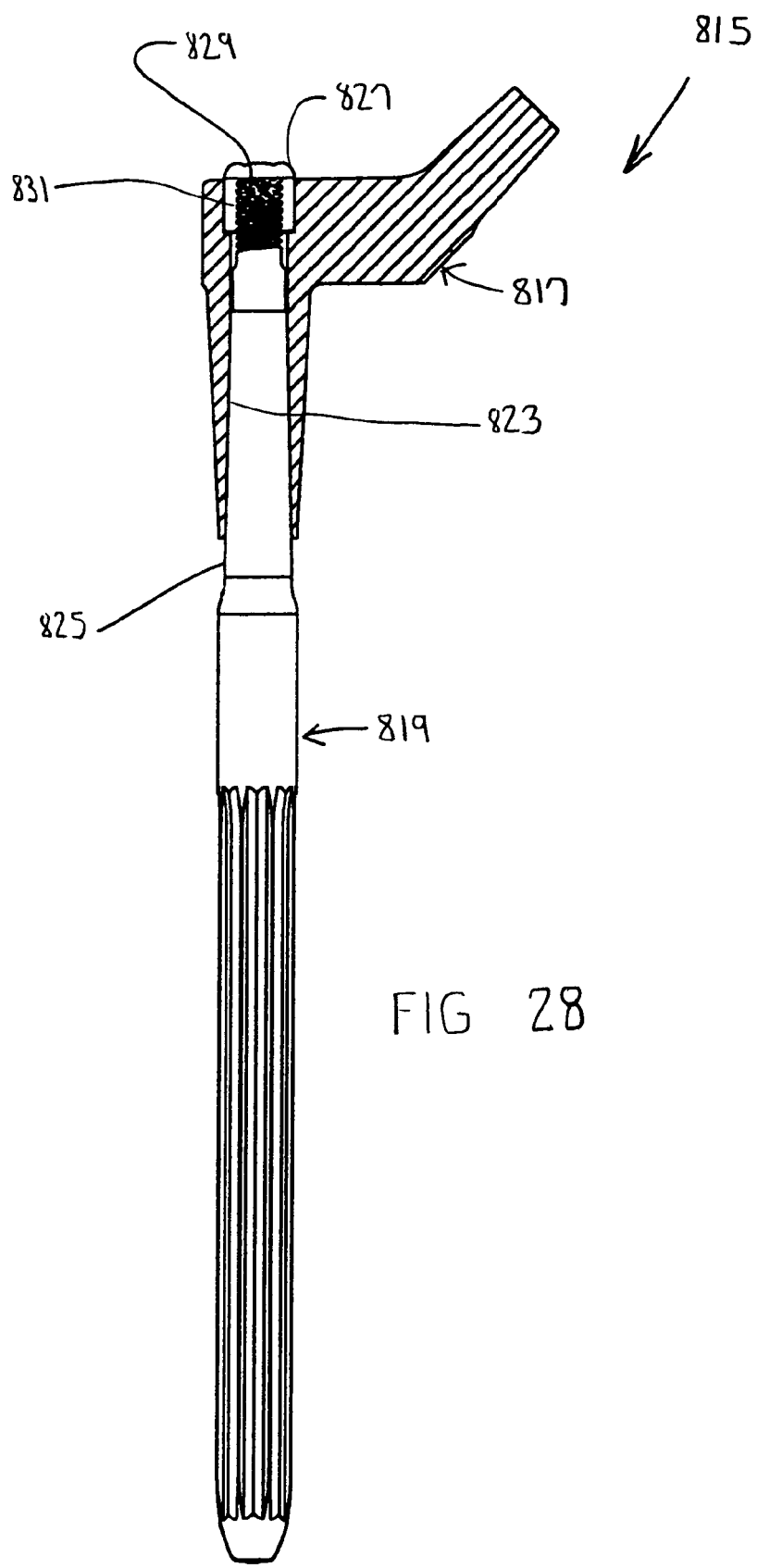
FIG. 28 is a plan view partially in cross section of the modular hip stem of FIG. 26.

While the internal taper 823 of the proximal body and the external taper 825 of the distal stem may provide a sufficiently secure connection, referring now to FIG. 28, the prosthesis 815 may further include a nut 827 which includes internal threads 829 which mate with external threads 831 on the distal stem to further secure the proximal body 817 to the distal stem 819.

Figure 29:
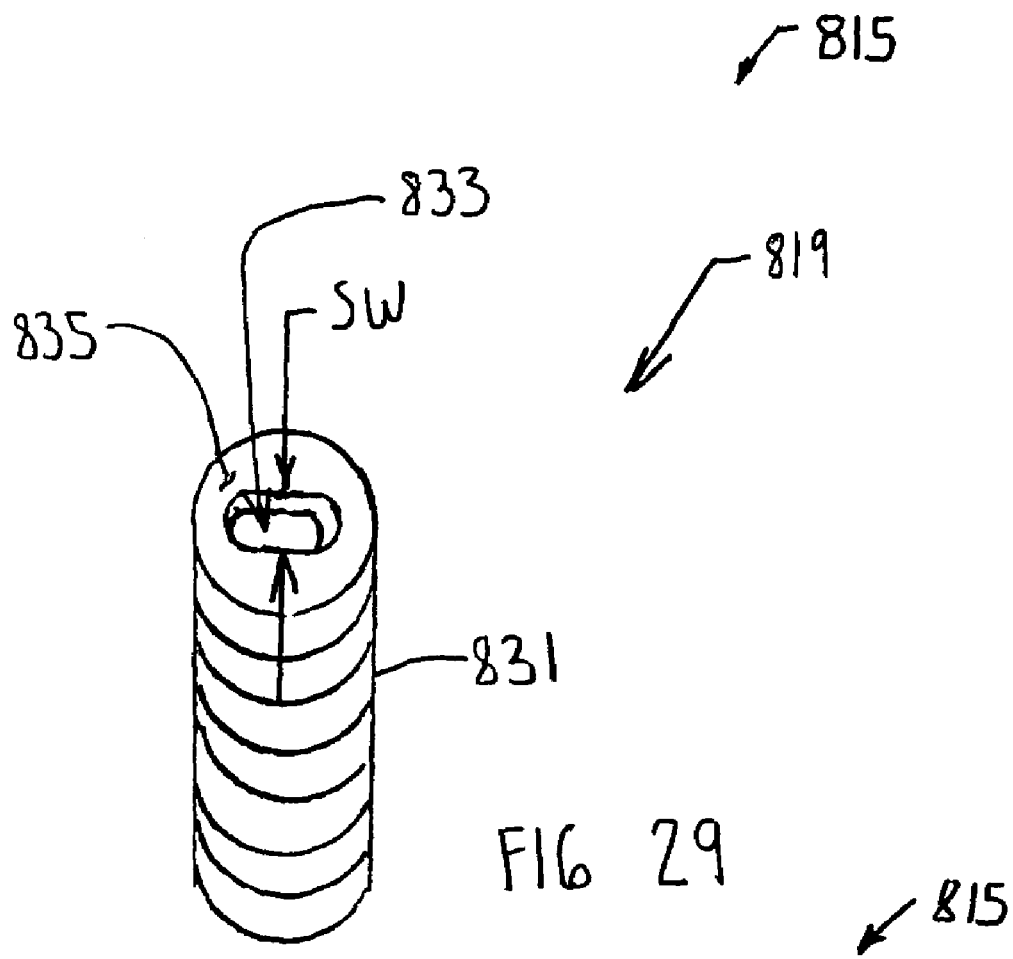
FIG. 29 is a partial perspective view of the threaded end of the modular hip stem of FIG. 26.
Figure 30:
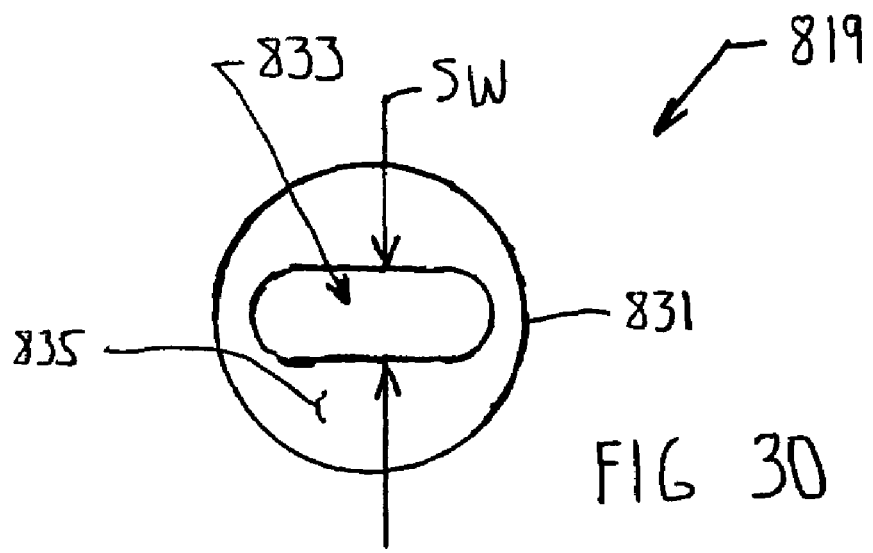
FIG. 30 is a partial top view of the threaded end of the prosthesis of the modular hip stem of FIG. 26.

Referring now to FIGS. 29 and 30, the portion of the distal stem 819 adjacent proximal end 835 is shown in greater detail. As shown in FIGS. 29 and 30, a recessed slot 833 is formed on the proximal end 835 of the distal stem 819. The slot 833 has a width SW that is similar to the width of the slot 32 of the reamer 2 (see FIG. 4).

Figure 31:
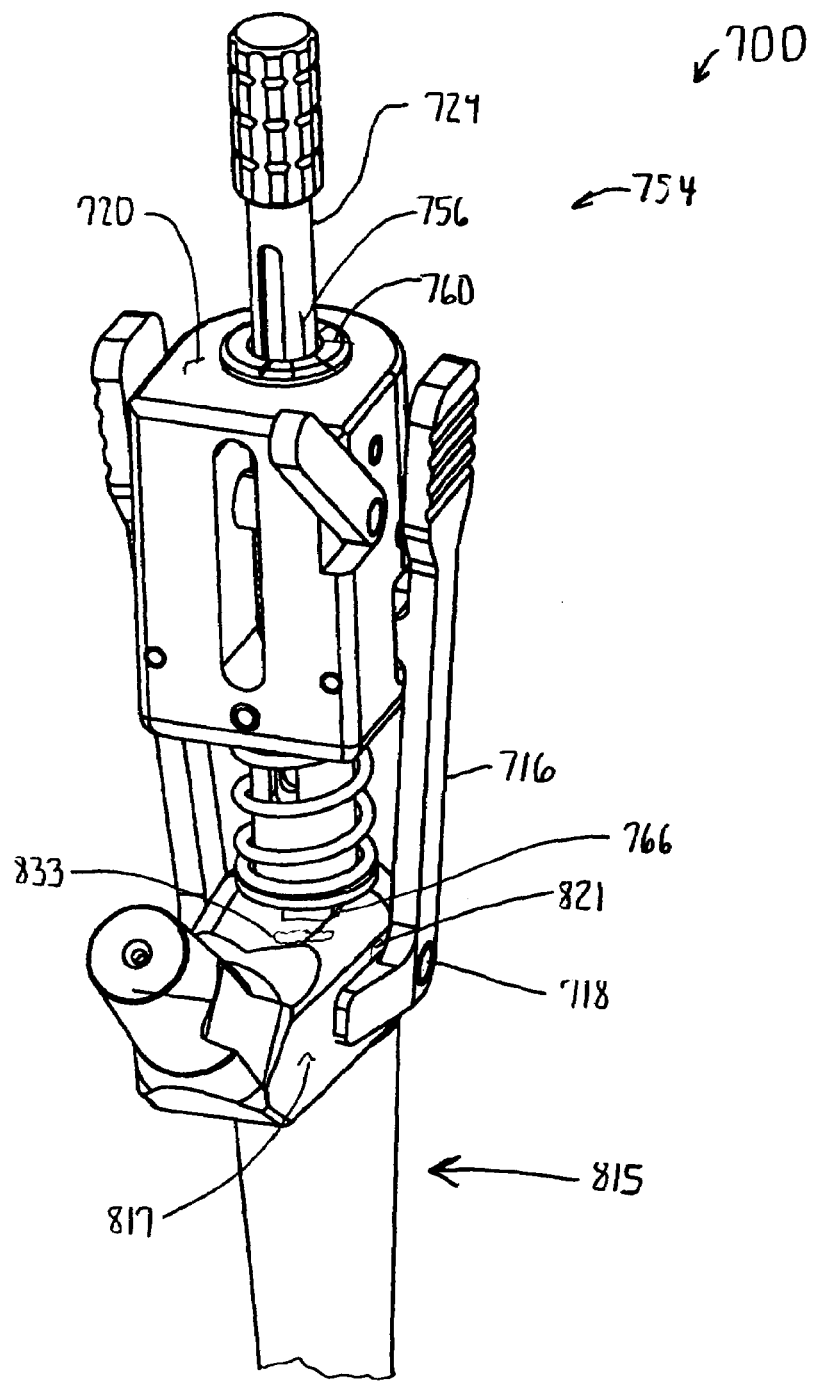
FIG. 31 is a perspective view of the alignment tool of FIG. 25 shown in use for aligning the stem of FIG. 26 to correspond to the alignment of the trial assembly of FIG. 10 shown with the hip stem in position.

Referring now to FIG. 31, the alignment device 700 is shown in position on the prosthesis 815. The alignment device 700 is positioned over a prosthesis 815 with the tang 766 of the alignment device 700 in position engaging the slot 833 of the prosthesis 815. Similarly the pins 718 and the arms 716 of the alignment device 700 are positioned in holes 821 in the body 817 of the implant 815. The distal stem 819 is rotated with respect to the proximal body 817 until the alignment mark 756 located on the rod 724 is alignment with the mark 760 on the body 720 of the alignment device 700. When the alignment marks 756 and 760 are in alignment, the orientation of the prosthesis 815 is corresponding to the alignment of the trial 12.

It should be appreciated that since the reamer 2 is straight with a circular cross section the alignment device 700 may not be required to orient the reamer 2 to trial 12. Also, since the distal stem 819 may be straight with a circular cross section the alignment device 700 may not be required to orient the proximal body to distal trial 819. Orientation by sight or by marking the patient is advised to replicate orientation of the trial 12 on implant 815.

After the proximal body 817 and the distal 819 are properly aligned, the proximal body 817 needs to be securely fastened to the distal stem 819. This securement is first done providing sufficient axial force to properly seat the distal stem 819 to the proximal body 817.

Figure 32:
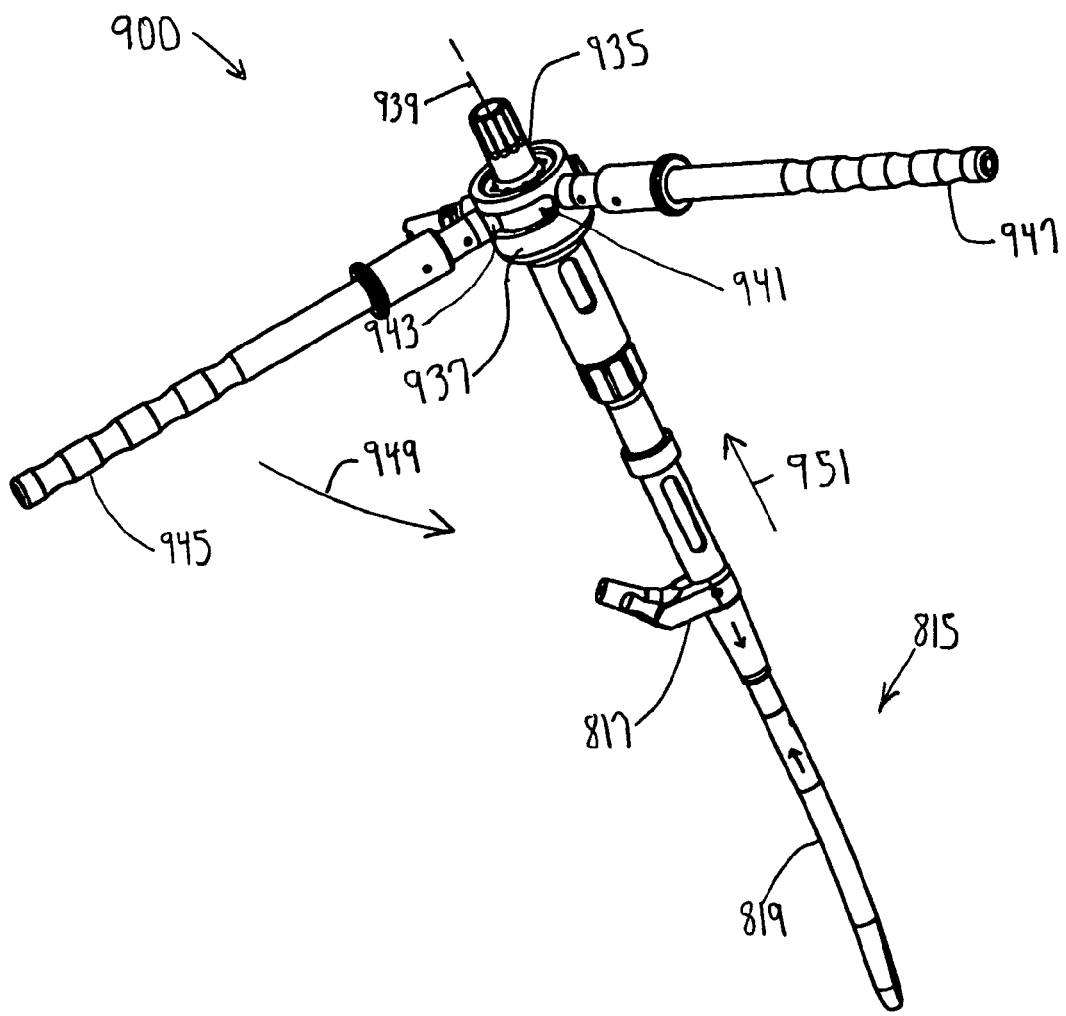
FIG. 32 is a perspective view of an assembly tool shown in use for assembling the stem of FIG. 26.

Referring now to FIG. 32, an assembly device for use in assuring that the proximal body and distal stem of a prosthesis for use with the reamer of the present invention may be properly secured is shown as assembly device 900. Assembly 900 includes a second member 935 in the form of a rod. The second member 935 may be, for example, threadably securable to distal stem 819 of the implant 815.

The assembly device may further include a first member 937 in the form of a hollow tube. The first member 937 is slidably fitted along longitudinal axis 939 with respect to the second member 935. The first member 937 may be engaged with the proximal body 817 of the implant 815. For example, opposing ends of the first member 937 and the proximal body 817 may be physically mated. An arcuate slot 941 formed in the first member 937 may restrainably guide a pin 943 extending from the second member 935.

An actuating arm 945 may be secured to the end of the pin 943 and a restraining arm 947 may be secured to the first member 937. As the actuating arm 945 is rotated in the direction of arrow 949, the second member 935 is urged in the direction of arrow 951 with respect to the first member 937. Once the second member 935 is connected to the distal stem 819, the implant 815 likewise moves in the direction of arrow 951 with respect to the proximal body 817, thereby properly securing the distal stem 819 to the proximal body 817 of the implant 815.

Figure 33:
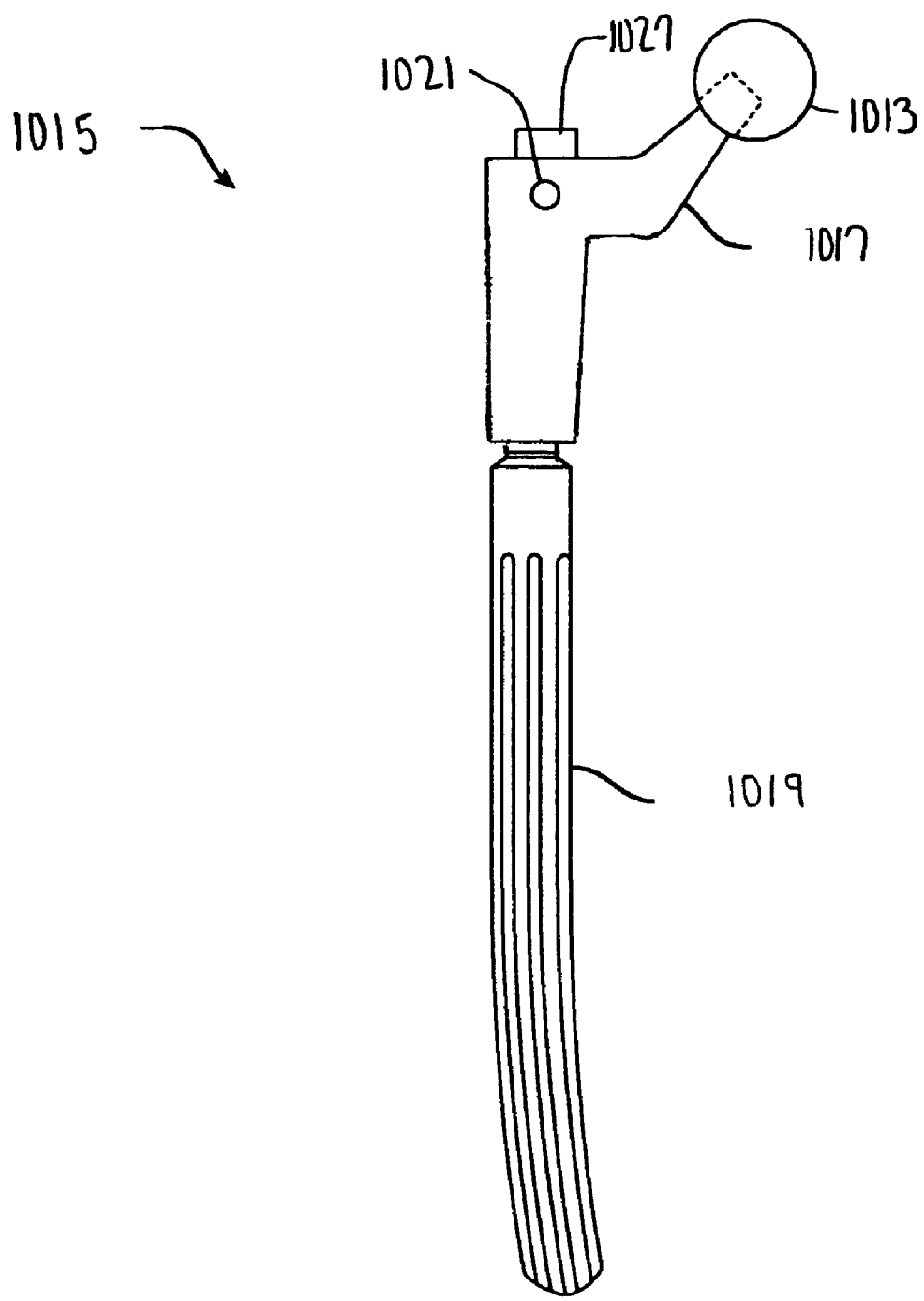
FIG. 33 is a plan view of a second embodiment of a modular hip stem implant.
Figure 34:
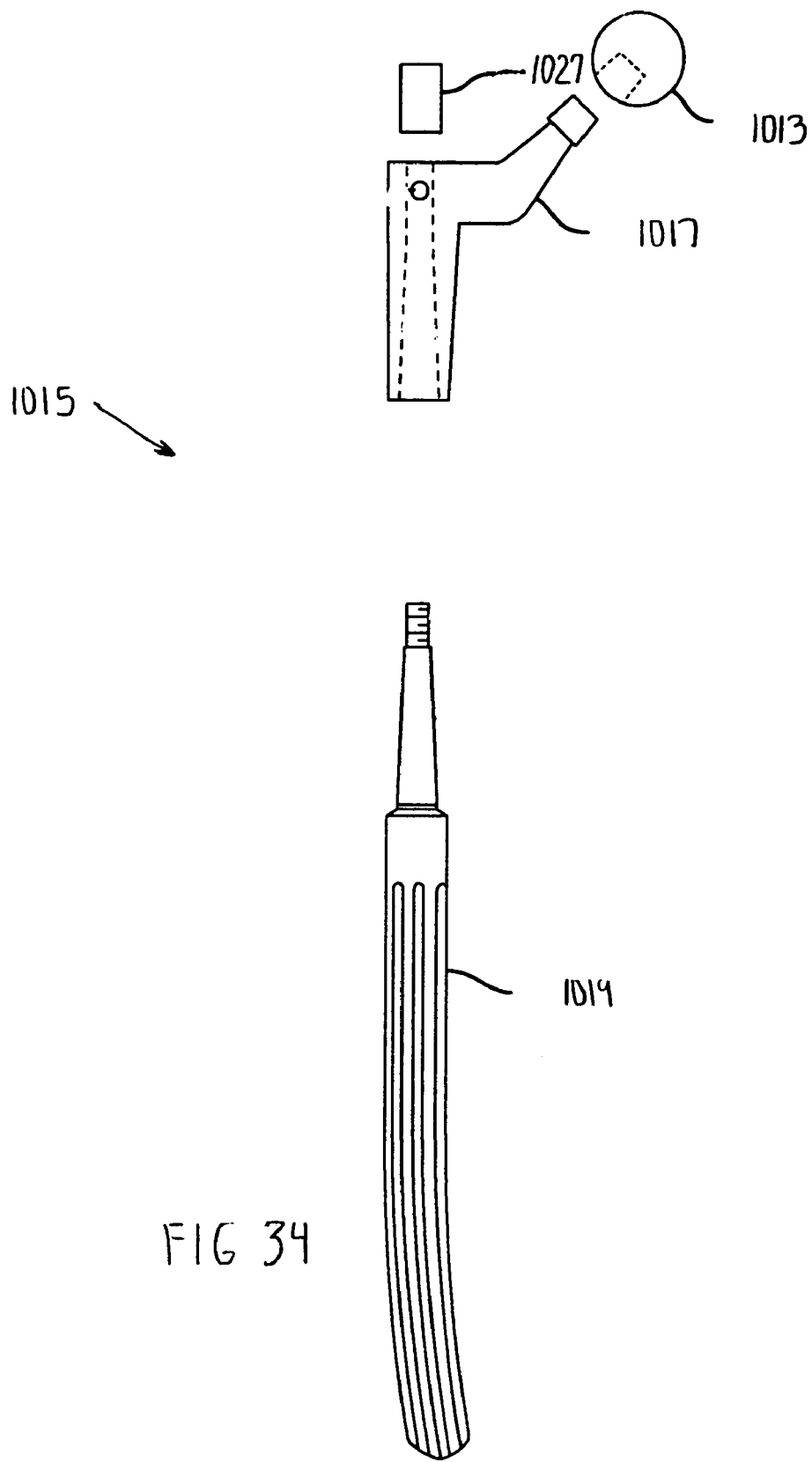
FIG. 34 is an exploded plan view of the modular hip stem implant of FIG. 33.

Referring now to FIGS. 33 and 34, another embodiment of a prosthesis for use with the reamer of the present invention is shown as implant or prosthesis 1015. The prosthesis 1015 includes a proximal body 1017 which is secured to a distal stem 1019. Holes 1021 are formed on the proximal body 1017 and a nut 1027 is further used to secure the distal stem 1019 to the proximal body 1017. A head 1013 is attached to the proximal body 1017.

Figure 26:
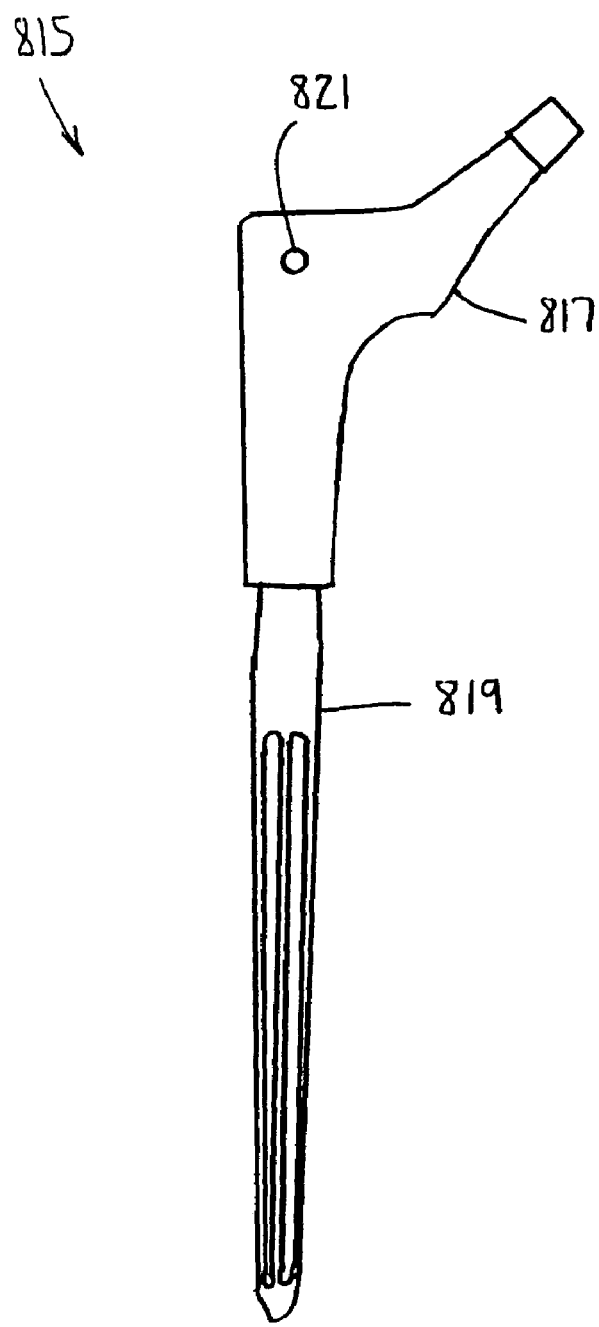
FIG. 26 is a plan view of an embodiment of a modular hip stem for use in the medullary canal of a femur prepared by the modular reamer assembly of FIG. 1.

The prosthesis 1015 is different than the prosthesis 815 of FIG. 26 in that the distal stem 1019 of the prosthesis 1015 has a genuinely curved or arcuate shape. The distal stem 1019 is utilized to extend further into the medullary canal of, for example, a long bone. The medullary canal of a long bone, particularly that of a femur, being curved or arcuate and thus the distal stem 1019 conforms to the medullary canal of the femur.

Figure 35:
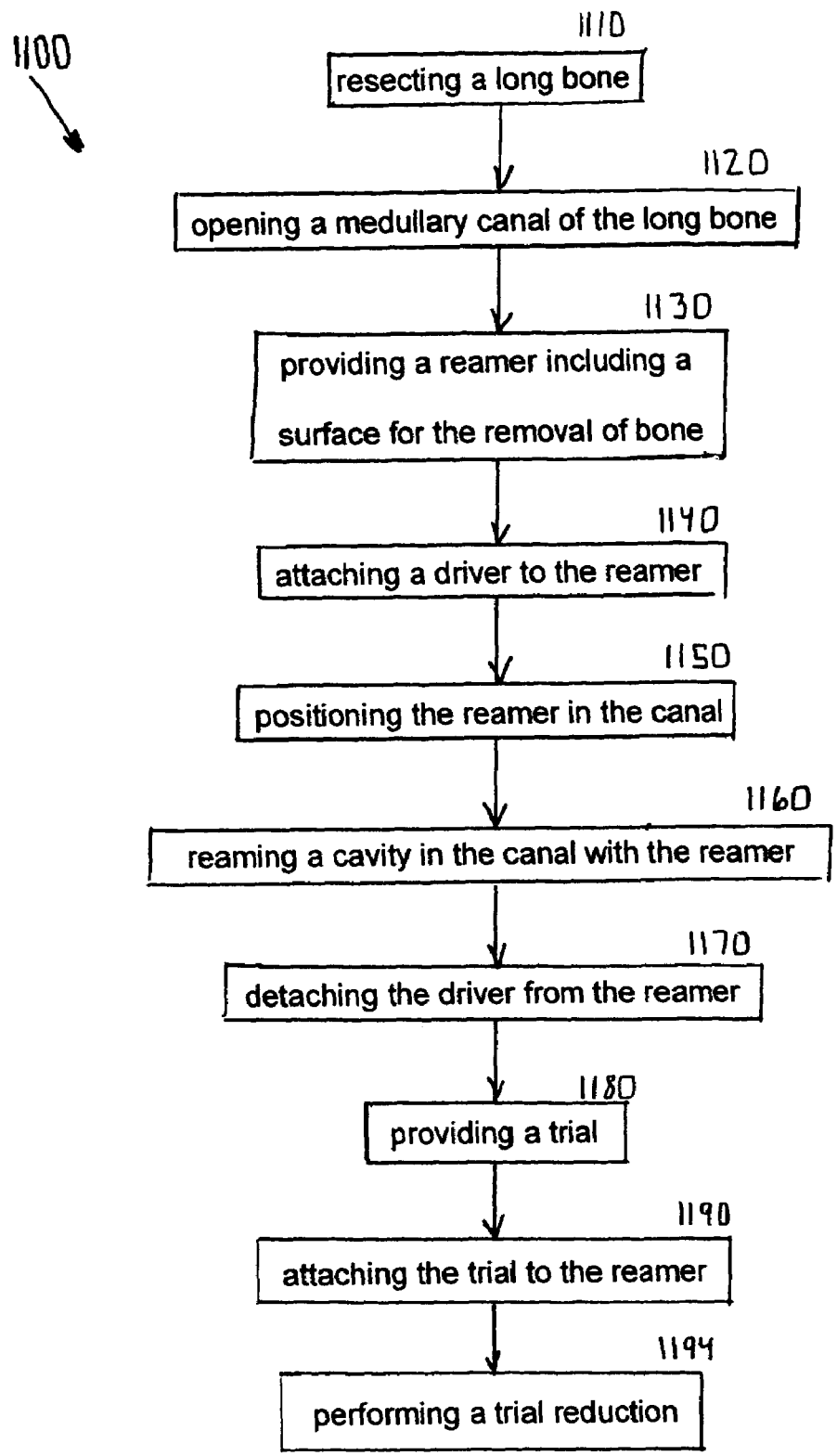
FIG. 35 is a flow chart of a surgical procedure according to the present invention utilizing a modular reamer.

Referring now to FIG. 35, another embodiment of the present invention is shown as surgical procedure or method 1100. The method 1100 includes a first step 1110 of resecting a long bone. The method 1100 further includes a second step 1120 of opening a medullary canal of the long bone. The method 1100 further includes a third step 1130 of providing a reamer including a surface for the removal of bone. The method 1100 further includes a fourth step 1140 of attaching a driver to the reamer and a fifth step 1150 of positioning the reamer in the canal. The method 1100 further includes a sixth step 1160 of reaming a cavity in the canal with the reamer. The method 1100 further includes a seventh step 1170 of detaching the driver from the reamer and an eighth step 1180 of providing a trial. The method 1100 further includes a ninth step 1190 of attaching the trial to the reamer and a tenth step 1194 of performing a trial reduction.

Referring now to FIGS. 36 and 37, a wrench 1200 is shown for use with the trial 12. The wrench 1200 includes a cylindrical body 1210 and a pair of cylindrical pins 1220 extending in an opposed orientation near an end 1230 of the wrench 1200. The body 1210 may include knurls 1240 on periphery 1250 of the wrench.

Referring now to FIGS. 15, 36 and 37, the periphery 1250 of the wrench 1200 is preferably sized to slidably fit within the opening 91 of the nut 82. The pins 1220 are designed to slidably fit in the axial slots 96 of the nut 82. Thus, as the wrench 1200 is rotated the nut 82 is similarly rotated.

Although the present invention and its advantages have been described in detail, it should be understood that various changes, substitutions, and alterations can be made therein without departing from the spirit and scope of the present invention as defined by the appended claims.

We claim:

1. A kit for use with a driver in performing joint arthroplasty, said kit comprising:
    a trial; and
    a reamer for preparing a cavity in the intramedullary canal of a long bone to assist in performing a trial reduction, the reamer including a first portion for placement at least partially in the cavity of the long bone and a second portion operably connected to the first portion, said second portion being removably connectable to the driver, said trial being removably attachable to said reamer, wherein said reamer includes a part thereof having a tapered external periphery wherein the driver includes a part thereof having a tapered internal periphery, and wherein said trial includes a portion thereof having a tapered internal periphery thereof.

2. A kit for use in performing hip joint arthroplasty, said kit to be utilized to prepare a cavity in the femoral canal of a femur with the use of a driver and to assist in performing a trial reduction, said kit comprising:
    a hip femoral component trial; and
    a reamer for preparation of the cavity in the femoral canal, said reamer including a first portion for placement at least partially in the cavity of the femur and a second portion connectable to the driver, said trial and the driver being removably attachable to said reamer, so that the said reamer and the driver can be assembled to prepare the cavity and so that said reamer and said trial can be assembled to form a hip femoral component trial assembly without the removal of said reamer from the cavity, wherein said reamer includes a part thereof having a tapered external periphery, wherein the driver includes a part thereof having a tapered internal periphery, and wherein said trial includes a portion thereof having a tapered internal periphery thereof.

3. A method for providing joint arthroplasty comprising:
resecting a long bone;
opening a medullary canal of the long bone;
providing a reamer including a surface for the removal of bone;
attaching a driver to the reamer;
positioning the reamer in the canal;
reaming a cavity in the canal with the reamer;
detaching the driver from the reamer;
providing a trial;
attaching the trial to the reamer; and
performing a trial reduction, wherein the providing the reamer step comprises providing a reamer with the reamer having an externally tapered shaft, wherein the attaching the driver step comprises attaching a driver having an internally tapered shaft to the externally tapered shaft of the reamer, and wherein the providing the trial step comprises providing a trial having an internally tapered shaft fitted to the externally tapered shaft of the reamer.

* * * * *